United States Patent
Lee et al.

(10) Patent No.: US 8,361,984 B2
(45) Date of Patent: Jan. 29, 2013

(54) SMALL INTERFERING RNAS AND METHODS FOR PREVENTION, INHIBITION AND/OR TREATMENT OF MALIGNANT PROGRESSION OF BREAST CANCER

(75) Inventors: Chia-Hwa Lee, Taipei (TW); Ching-Shui Huang, Taipei (TW); Ching-Shyang Chen, Taipei (TW); Shih-Hsin Tu, Taipei (TW); Ying-Jan Wang, Taipei (TW); Yu-Jia Chang, Taipei (TW); Ka-Wai Tam, Taipei (TW); Po-Li Wei, Taipei (TW); Tzu-Chun Cheng, Taipei (TW); Jan-Show Chu, Taipei (TW); Li-Ching Chen, Taipei (TW); Chih-Hsiung Wu, Taipei (TW); Yuan-Soon Ho, Taipei (TW)

(73) Assignee: Taipei Medical University, Taipei (TW)

( * ) Notice: Subject to any disclaimer, the term of this patent is extended or adjusted under 35 U.S.C. 154(b) by 58 days.

(21) Appl. No.: 13/027,038

(22) Filed: Feb. 14, 2011

(65) Prior Publication Data

US 2012/0207817 A1 Aug. 16, 2012

(51) Int. Cl.
*A61K 31/70* (2006.01)
*C07H 21/02* (2006.01)
*C07H 21/04* (2006.01)

(52) U.S. Cl. .............. 514/44 A; 536/23.1; 536/24.5

(58) Field of Classification Search .......... 514/44; 536/23.1, 24.5
See application file for complete search history.

(56) References Cited

PUBLICATIONS

Jianxun Mei et al., Transformation of non-cancerous human breast epithelial cell line MCF10A by the tobacco-specific carcinogen NNK, Breast Cancer Research and Treatment, 2003, pp. 95-105, vol. 79, Netherlands.
Nalin Siriwardhana et al., Precancerous model of human breast epithelial cells induced by NNK or prevention, Breast Cancer Res Treat, 2008, pp. 427-441, vol. 109.
Kip A. West et al., Rapid Akt activation by nicotine and a tobacco carcinogen modulates the phenotype of normal human airway epithelial cells, The Journal of Clinical Investigation, Jan. 2003, pp. 81-90, vol. 111, No. 1.
Richard D. Egleton et al., Nicotine acetylcholine receptors in cancer: multiple roles in proliferation and inhibition of apoptosis, Trends in Pharmacological Sciences, pp. 151-158, 2007, vol. 29, No. 3.
Hildegard M. Schuller et al., Nitrosamines as nicotinic receptor ligands, Life Sciences, 2007, pp. 2274-2280, vol. 80.
Hildegard M. Schuller et al., Tobacco-Specific Carcinogenic Nitrosamines: Ligands for Nicotinic Acetylcholine Receptors in Human Lung Cancer Cells, Biochemical Pharmacology, 1998, pp. 1377-1384, vol. 55.
Helen Pui Shan Wong et al., Nicotine Promotes Colon Tumor Growth and Angiogenesis through B-Adrenergic Activation, Toxicological Sciences, 2007, pp. 279-287, vol. 97, No. 2.
Michelle Vincler et al., Molecular mechanism for analgesia invovlving specific antagonism of α9α10 nicotinic acetylcholine receptors, PNAS, Nov. 21, 2006, pp. 17880-17884, vol. 103, No. 47.
S. T. Nevin et al., Are α9α10 Nicotinic Acetylcholine Receptors a Pain Target for a-Conotoxins?, Mol Pharmacol, 2007, pp. 1406-1410, vol. 72, USA.

(Continued)

*Primary Examiner* — Terra Cotta Gibbs
(74) *Attorney, Agent, or Firm* — WPAT, P.C.; Anthony King

(57) ABSTRACT

The invention found that overexpression and activation of α9-nAChR are associated with tumorigenesis of breast cancer and create a number of small interfering RNAs to inhibit the expression of α9-nAChR so as to inhibit breast cancer. Therefore, the invention provides small interfering RNAs (siRNAs) for inhibiting expression of α9-nAChR so as to inhibit breast cancer, methods to prevent/inhibit/treat malignant progression of nicotine-derived-compound-induced breast cancer and method of determining malignant level of such breast cancer.

13 Claims, 20 Drawing Sheets

PUBLICATIONS

Rong-Jane Chen et al., Rapid Activation of Stat3 and ERK1/2 by Nicotine Modulates Cell Proliferation in Human Bladder Cancer Cells, Toxicological Sciences, 2008, pp. 283-293, vol. 104, No. 2.

Yung-Leun Shih et al., Combination Treatment with Luteolin and Quercetin Enhances Antiproliferative Effects in Nicotine-Treated MDA-MB-231 Cells by Down-regulating Nicotinic Acetylcholine Receptors, Journal of Agricultural and Food Chemistry, 2010, pp. 235--241, vol. 58, No. 1.

Chia-Hwa Lee et al., Overexpression and Activation of the a9-Nicotinic Receptor During Tumorigenesis in Human Breast Epithelial Cells, Journal of the National Cancer Institute, Sep. 8, 2010, pp. 1322-1335, vol. 102, Issue 17.

Chia-Hwa Lee et al., Crosstalk between nicotine and estrogen-induced estrogen receptor activation induces a9-nicotinic acetylcholine receptor expression in human breast cancer cells, Breast Cancer Res Treat, Oct. 16, 2010.

Shih-Hsin Tu et al., Tea polyphenol (—)-epigallocatechin-3-gallate inhibits nicotine- and estrogen-induced a9-nicotinic acetylcholine receptor upregulation in human breast cancer cells, Mol. Nutr. Food Res., 2010, pp. 1-12, vol. 54.

Yung-Leun Shih et al., Combination Treatment with Luteolin and Quercetin Enhances Antiproliferative Effects in Nicotine-Treated MDA-MB-231 Cells by Down-regulating Nicotinic Acetylcholine Receptors, Journal of Agricultural and Food Chemistry, 2010, pp. 235-241, vol. 58, No. 1.

Ching-Shyang Chen et al., Nicotine-induced human breast cancer cell proliferation attenuated by garcinol through down-regulation of the nicotinic receptor and cyclin D3 proteins, Breast Cancer Res Treat, Mar. 13, 2010.

SEQUENCE LISTING

<160> NUMBER OF SEQ ID NOS: 58

<210> SEQ ID NO 1
<211> LENGTH: 19
<212> TYPE: DNA
<213> ORGANISM: Artificial Sequence
<220> FEATURE:

```
<223> OTHER INFORMATION: Synthetic oligonucleotide
<220> FEATURE:
<221> NAME/KEY: misc_feature
<222> LOCATION: (1)..(19)
<223> OTHER INFORMATION: siRNA

<400> SEQUENCE: 1
tgtgatctcc tatggctgc                                                    19

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: siRNA

<400> SEQUENCE: 2
acactagagg ataccgacg                                                    19

<210> SEQ ID NO 3
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: siRNA

<400> SEQUENCE: 3
aaagcagcca ggaacaaag                                                    19

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: siRNA

<400> SEQUENCE: 4
tttcgtcggt ccttgtttc                                                    19

<210> SEQ ID NO 5
<211> LENGTH: 47
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(47)
<223> OTHER INFORMATION: siRNA

<400> SEQUENCE: 5
tgtgatctcc tatggctgct tcaagagagc agccatagga gatcaca                     47

<210> SEQ ID NO 6
<211> LENGTH: 47
<212> TYPE: DNA
<213> ORGANISM: Artificial Sequence
<220> FEATURE:
```

```
<223> OTHER INFORMATION: Synthetic oligonucleotide
<220> FEATURE:
<221> NAME/KEY: misc_feature
<222> LOCATION: (1)..(47)
<223> OTHER INFORMATION: siRNA

<400> SEQUENCE: 6
acactagagg ataccgacga agttctctcg tcggtatcct ctagtgt                    47

<210> SEQ ID NO 7
<211> LENGTH: 47
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(47)
<223> OTHER INFORMATION: siRNA

<400> SEQUENCE: 7
aaagcagcca ggaacaaagt tcaagagact ttgttcctgg ctgcttt                    47

<210> SEQ ID NO 8
<211> LENGTH: 47
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(47)
<223> OTHER INFORMATION: siRNA

<400> SEQUENCE: 8
tttcgtcggt ccttgtttca agttctctga acaaggacc gacgaaa                    47

<210> SEQ ID NO 9
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: loop sequence

<400> SEQUENCE: 9 ttcaagaga                                                               9

<210> SEQ ID NO 10
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: loop sequence

<400> SEQUENCE: 10 tctcttgaa                                                               9

<210> SEQ ID NO 11
<211> LENGTH: 60
<212> TYPE: DNA
<213> ORGANISM: Artificial Sequence
<220> FEATURE:
```

```
<223> OTHER INFORMATION: Synthetic oligonucleotide
<220> FEATURE:
<221> NAME/KEY: misc_feature
<222> LOCATION: (1)..(60)
<223> OTHER INFORMATION: siRNA
<220> FEATURE:
<221> NAME/KEY: misc_feature
<222> LOCATION: (1)..(60)
<223> OTHER INFORMATION: Synthetic oligonucleotide having a hair loop
      and an overhang region

<400> SEQUENCE: 11
gatcccctgt gatctcctat ggctgcttca agagagcagc cataggagat cacatttttta    60

<210> SEQ ID NO 12
<211> LENGTH: 60
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(60)
<223> OTHER INFORMATION: siRNA
<220> FEATURE:
<221> NAME/KEY: misc_feature
<222> LOCATION: (1)..(60)
<223> OTHER INFORMATION: Synthetic oligonucleotide having a hair loop
      and an overhang region

<400> SEQUENCE: 12
agcttaaaaa tgtgatctcc tatggctgct ctcttgaagc agccatagga gatcacaggg    60

<210> SEQ ID NO 13
<211> LENGTH: 60
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(60)
<223> OTHER INFORMATION: Synthetic oligonucleotide having a hair loop
      and an overhang region

<400> SEQUENCE: 13
gatccccaaa gcagccagga acaaagttca agagactttg ttcctggctg ctttttttta    60

<210> SEQ ID NO 14
<211> LENGTH: 60
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(60)
<223> OTHER INFORMATION: Synthetic oligonucleotide having a hair loop
      and an overhang region

<400> SEQUENCE: 14
agcttaaaaa aaagcagcca ggaacaaagt ctcttgaact tgttcctgg ctgctttggg    60

<210> SEQ ID NO 15
<211> LENGTH: 17
<212> TYPE: DNA
<213> ORGANISM: Artificial Sequence
<220> FEATURE:
<223> OTHER INFORMATION: nAchR \1-F primer
<220> FEATURE:
<221> NAME/KEY: misc_feature
<222> LOCATION: (1)..(17)
```

-continued

<223> OTHER INFORMATION: Synthetic oligonucleotide for RT-PCR

<400> SEQUENCE: 15
cgtctggtgg caaagct                                                    17

<210> SEQ ID NO 16
<211> LENGTH: 17
<212> TYPE: DNA
<213> ORGANISM: Artificial Sequence
<220> FEATURE:
<223> OTHER INFORMATION: nAchR \1-R primer
<220> FEATURE:
<221> NAME/KEY: misc_feature
<222> LOCATION: (1)..(17)
<223> OTHER INFORMATION: Synthetic oligonucleotide for RT-PCR

<400> SEQUENCE: 16
ccgctctcca tgaagtt                                                    17

<210> SEQ ID NO 17
<211> LENGTH: 17
<212> TYPE: DNA
<213> ORGANISM: Artificial Sequence
<220> FEATURE:
<223> OTHER INFORMATION: nAchR \2-F primer
<220> FEATURE:
<221> NAME/KEY: misc_feature
<222> LOCATION: (1)..(17)
<223> OTHER INFORMATION: Synthetic oligonucleotide for RT-PCR

<400> SEQUENCE: 17
ccggtggctt ctgatga                                                    17

<210> SEQ ID NO 18
<211> LENGTH: 18
<212> TYPE: DNA
<213> ORGANISM: Artificial Sequence
<220> FEATURE:
<223> OTHER INFORMATION: nAchR \2-R primer
<220> FEATURE:
<221> NAME/KEY: misc_feature
<222> LOCATION: (1)..(18)
<223> OTHER INFORMATION: Synthetic oligonucleotide for RT-PCR

<400> SEQUENCE: 18
cagatcattc cagctagg                                                   18

<210> SEQ ID NO 19
<211> LENGTH: 17
<212> TYPE: DNA
<213> ORGANISM: Artificial Sequence
<220> FEATURE:
<223> OTHER INFORMATION: nAchR \3-F primer
<220> FEATURE:
<221> NAME/KEY: misc_feature
<222> LOCATION: (1)..(17)
<223> OTHER INFORMATION: Synthetic oligonucleotide for RT-PCR

<400> SEQUENCE: 19
ccatgtctca gctggtg                                                    17

<210> SEQ ID NO 20
<211> LENGTH: 18
<212> TYPE: DNA
<213> ORGANISM: Artificial Sequence
<220> FEATURE:
<223> OTHER INFORMATION: nAchR \3-R primer
<220> FEATURE:
<221> NAME/KEY: misc_feature
<222> LOCATION: (1)..(18)

```
<223> OTHER INFORMATION: Synthetic oligonucleotide for RT-PCR

<400> SEQUENCE: 20
gtccttgagg ttcatgga                                                      18

<210> SEQ ID NO 21
<211> LENGTH: 22
<212> TYPE: DNA
<213> ORGANISM: Artificial Sequence
<220> FEATURE:
<223> OTHER INFORMATION: nAchR \4-F primer
<220> FEATURE:
<221> NAME/KEY: misc_feature
<222> LOCATION: (1)..(22)
<223> OTHER INFORMATION: Synthetic oligonucleotide for RT-PCR

<400> SEQUENCE: 21
gaatgtcacc tccatccgca tc                                                 22

<210> SEQ ID NO 22
<211> LENGTH: 21
<212> TYPE: DNA
<213> ORGANISM: Artificial Sequence
<220> FEATURE:
<223> OTHER INFORMATION: nAchR \4-R primer
<220> FEATURE:
<221> NAME/KEY: misc_feature
<222> LOCATION: (1)..(21)
<223> OTHER INFORMATION: Synthetic oligonucleotide for RT-PCR

<400> SEQUENCE: 22
ccggcaattg tccttgacca c                                                  21

<210> SEQ ID NO 23
<211> LENGTH: 19
<212> TYPE: DNA
<213> ORGANISM: Artificial Sequence
<220> FEATURE:
<223> OTHER INFORMATION: nAchR \5-F primer
<220> FEATURE:
<221> NAME/KEY: misc_feature
<222> LOCATION: (1)..(19)
<223> OTHER INFORMATION: Synthetic oligonucleotide for RT-PCR

<400> SEQUENCE: 23
tcatgtagac aggtacttc                                                     19

<210> SEQ ID NO 24
<211> LENGTH: 20
<212> TYPE: DNA
<213> ORGANISM: Artificial Sequence
<220> FEATURE:
<223> OTHER INFORMATION: nAchR \5-R primer
<220> FEATURE:
<221> NAME/KEY: misc_feature
<222> LOCATION: (1)..(20)
<223> OTHER INFORMATION: Synthetic oligonucleotide for RT-PCR

<400> SEQUENCE: 24
atttgcccat ttataaataa                                                    20

<210> SEQ ID NO 25
<211> LENGTH: 18
<212> TYPE: DNA
<213> ORGANISM: Artificial Sequence
<220> FEATURE:
<223> OTHER INFORMATION: nAchR \6-F primer
<220> FEATURE:
<221> NAME/KEY: misc_feature
<222> LOCATION: (1)..(18)
```

<223> OTHER INFORMATION: Synthetic oligonucleotide for RT-PCR

<400> SEQUENCE: 25
ggcctctgga caagacaa                                                        18

<210> SEQ ID NO 26
<211> LENGTH: 19
<212> TYPE: DNA
<213> ORGANISM: Artificial Sequence
<220> FEATURE:
<223> OTHER INFORMATION: nAchR \6-R primer
<220> FEATURE:
<221> NAME/KEY: misc_feature
<222> LOCATION: (1)..(19)
<223> OTHER INFORMATION: Synthetic oligonucleotide for RT-PCR

<400> SEQUENCE: 26
aagattttcc tgtgttccc                                                       19

<210> SEQ ID NO 27
<211> LENGTH: 30
<212> TYPE: DNA
<213> ORGANISM: Artificial Sequence
<220> FEATURE:
<223> OTHER INFORMATION: nAchR \7-F primer
<220> FEATURE:
<221> NAME/KEY: misc_feature
<222> LOCATION: (1)..(30)
<223> OTHER INFORMATION: Synthetic oligonucleotide for RT-PCR

<400> SEQUENCE: 27
cacagtggcc ctgcagaccg atggtacgga                                           30

<210> SEQ ID NO 28
<211> LENGTH: 30
<212> TYPE: DNA
<213> ORGANISM: Artificial Sequence
<220> FEATURE:
<223> OTHER INFORMATION: nAchR \7-R primer
<220> FEATURE:
<221> NAME/KEY: misc_feature
<222> LOCATION: (1)..(30)
<223> OTHER INFORMATION: Synthetic oligonucleotide for RT-PCR

<400> SEQUENCE: 28
ctcagtggcc ctgctgaccg atggtacgga                                           30

<210> SEQ ID NO 29
<211> LENGTH: 18
<212> TYPE: DNA
<213> ORGANISM: Artificial Sequence
<220> FEATURE:
<223> OTHER INFORMATION: nAchR \9-F primer
<220> FEATURE:
<221> NAME/KEY: misc_feature
<222> LOCATION: (1)..(18)
<223> OTHER INFORMATION: Synthetic oligonucleotide for RT-PCR

<400> SEQUENCE: 29
gtccagggtc ttgtttgt                                                        18

<210> SEQ ID NO 30
<211> LENGTH: 18
<212> TYPE: DNA
<213> ORGANISM: Artificial Sequence
<220> FEATURE:
<223> OTHER INFORMATION: nAchR \9-R primer
<220> FEATURE:
<221> NAME/KEY: misc_feature
<222> LOCATION: (1)..(18)

<223> OTHER INFORMATION: Synthetic oligonucleotide for RT-PCR

<400> SEQUENCE: 30
atccgctctt gctatgat                                                 18

<210> SEQ ID NO 31
<211> LENGTH: 18
<212> TYPE: DNA
<213> ORGANISM: Artificial Sequence
<220> FEATURE:
<223> OTHER INFORMATION: nAchR \10-F primer
<220> FEATURE:
<221> NAME/KEY: misc_feature
<222> LOCATION: (1)..(18)
<223> OTHER INFORMATION: Synthetic oligonucleotide for RT-PCR

<400> SEQUENCE: 31
ctgttccgtg acctctttt                                                18

<210> SEQ ID NO 32
<211> LENGTH: 18
<212> TYPE: DNA
<213> ORGANISM: Artificial Sequence
<220> FEATURE:
<223> OTHER INFORMATION: nAchR \10-R primer
<220> FEATURE:
<221> NAME/KEY: misc_feature
<222> LOCATION: (1)..(18)
<223> OTHER INFORMATION: Synthetic oligonucleotide for RT-PCR

<400> SEQUENCE: 32
ggaaggctgc tacatcca                                                 18

<210> SEQ ID NO 33
<211> LENGTH: 19
<212> TYPE: DNA
<213> ORGANISM: Artificial Sequence
<220> FEATURE:
<223> OTHER INFORMATION: nAchR ]2-F primer
<220> FEATURE:
<221> NAME/KEY: misc_feature
<222> LOCATION: (1)..(19)
<223> OTHER INFORMATION: Synthetic oligonucleotide for RT-PCR

<400> SEQUENCE: 33 cggctcccctt ccaaacaca                                               19

<210> SEQ ID NO 34
<211> LENGTH: 23
<212> TYPE: DNA
<213> ORGANISM: Artificial Sequence
<220> FEATURE:
<223> OTHER INFORMATION: nAchR ]2-R primer
<220> FEATURE:
<221> NAME/KEY: misc_feature
<222> LOCATION: (1)..(23)
<223> OTHER INFORMATION: Synthetic oligonucleotide for RT-PCR

<400> SEQUENCE: 34
gcaatgatgg cgtggctgct gca                                           23

<210> SEQ ID NO 35
<211> LENGTH: 18
<212> TYPE: DNA
<213> ORGANISM: Artificial Sequence
<220> FEATURE:
<223> OTHER INFORMATION: nAchR ]3-F primer
<220> FEATURE:
<221> NAME/KEY: misc_feature
<222> LOCATION: (1)..(18)

-continued

<223> OTHER INFORMATION: Synthetic oligonucleotide for RT-PCR

<400> SEQUENCE: 35
agaggctctt tctgcaga                                          18

<210> SEQ ID NO 36
<211> LENGTH: 18
<212> TYPE: DNA
<213> ORGANISM: Artificial Sequence
<220> FEATURE:
<223> OTHER INFORMATION: nAchR ]3-R primer
<220> FEATURE:
<221> NAME/KEY: misc_feature
<222> LOCATION: (1)..(18)
<223> OTHER INFORMATION: Synthetic oligonucleotide for RT-PCR

<400> SEQUENCE: 36
gccacatctt caaagcag                                          18

<210> SEQ ID NO 37
<211> LENGTH: 18
<212> TYPE: DNA
<213> ORGANISM: Artificial Sequence
<220> FEATURE:
<223> OTHER INFORMATION: nAchR ]4-F primer
<220> FEATURE:
<221> NAME/KEY: misc_feature
<222> LOCATION: (1)..(18)
<223> OTHER INFORMATION: Synthetic oligonucleotide for RT-PCR

<400> SEQUENCE: 37
ctgaaacagg aatggact                                          18

<210> SEQ ID NO 38
<211> LENGTH: 18
<212> TYPE: DNA
<213> ORGANISM: Artificial Sequence
<220> FEATURE:
<223> OTHER INFORMATION: nAchR ]4-R primer
<220> FEATURE:
<221> NAME/KEY: misc_feature
<222> LOCATION: (1)..(18)
<223> OTHER INFORMATION: Synthetic oligonucleotide for RT-PCR

<400> SEQUENCE: 38
ccatgtctat ctccgtgt                                          18

<210> SEQ ID NO 39
<211> LENGTH: 60
<212> TYPE: DNA
<213> ORGANISM: Artificial Sequence
<220> FEATURE:
<223> OTHER INFORMATION: nAchR \5 siRNA1-F primer
<220> FEATURE:
<221> NAME/KEY: misc_feature
<222> LOCATION: (1)..(60)
<223> OTHER INFORMATION: shRNA

<400> SEQUENCE: 39 gatccccccct gtattgggct ctcattttca agagaaatga gagcccaata caggttttta    60

<210> SEQ ID NO 40
<211> LENGTH: 60
<212> TYPE: DNA
<213> ORGANISM: Artificial Sequence
<220> FEATURE:
<223> OTHER INFORMATION: nAchR \5 siRNA1-R primer
<220> FEATURE:
<221> NAME/KEY: misc_feature
<222> LOCATION: (1)..(60)

```
<223> OTHER INFORMATION: shRNA

<400> SEQUENCE: 40
agcttaaaaa cctgtattgg gctctcattt ctcttgaaaa tgagagccca atacagggggg      60

<210> SEQ ID NO 41
<211> LENGTH: 60
<212> TYPE: DNA
<213> ORGANISM: Artificial Sequence
<220> FEATURE:
<223> OTHER INFORMATION: nAchR \5 siRNA2-F primer
<220> FEATURE:
<221> NAME/KEY: misc_feature
<222> LOCATION: (1)..(60)
<223> OTHER INFORMATION: shRNA

<400> SEQUENCE: 41 gatcccccccg tcttcgctat caacatttca agagaatgtt gatagcgaag acggttttta     60

<210> SEQ ID NO 42
<211> LENGTH: 60
<212> TYPE: DNA
<213> ORGANISM: Artificial Sequence
<220> FEATURE:
<223> OTHER INFORMATION: nAchR \5 siRNA2-R primer
<220> FEATURE:
<221> NAME/KEY: misc_feature
<222> LOCATION: (1)..(60)
<223> OTHER INFORMATION: shRNA

<400> SEQUENCE: 42
agcttaaaaa ccgtcttcgc tatcaacatt ctcttgaaat gttgatagcg aagacggggg      60

<210> SEQ ID NO 43
<211> LENGTH: 60
<212> TYPE: DNA
<213> ORGANISM: Artificial Sequence
<220> FEATURE:
<223> OTHER INFORMATION: nAchR \9SC siRNA1-F primer
<220> FEATURE:
<221> NAME/KEY: misc_feature
<222> LOCATION: (1)..(60)
<223> OTHER INFORMATION: shRNA

<400> SEQUENCE: 43
gatccccgag acgtgttcgc tttctcttca agagagagaa agcgaacacg tctcttttta      60

<210> SEQ ID NO 44
<211> LENGTH: 60
<212> TYPE: DNA
<213> ORGANISM: Artificial Sequence
<220> FEATURE:
<223> OTHER INFORMATION: nAchR \9 SC siRNA1-R primer
<220> FEATURE:
<221> NAME/KEY: misc_feature
<222> LOCATION: (1)..(60)
<223> OTHER INFORMATION: shRNA

<400> SEQUENCE: 44
agcttaaaaa gagacgtgtt cgctttctct ctcttgaaga gaaagcgaac acgtctcggg      60

<210> SEQ ID NO 45
<211> LENGTH: 60
<212> TYPE: DNA
<213> ORGANISM: Artificial Sequence
<220> FEATURE:
<223> OTHER INFORMATION: nAchR \9 SC siRNA2-F primer
<220> FEATURE:
<221> NAME/KEY: misc_feature
<222> LOCATION: (1)..(60)
```

```
<223> OTHER INFORMATION: shRNA

<400> SEQUENCE: 45
gatcccnggg aacaaacaag cacgaattca agagattcgt gcttgtttgt tccctttta      60

<210> SEQ ID NO 46
<211> LENGTH: 60
<212> TYPE: DNA
<213> ORGANISM: Artificial Sequence
<220> FEATURE:
<223> OTHER INFORMATION: nAchR \9 SC siRNA2-R primer
<220> FEATURE:
<221> NAME/KEY: misc_feature
<222> LOCATION: (1)..(60)
<223> OTHER INFORMATION: shRNA

<400> SEQUENCE: 46
agcttaaaaa gggaacaaac aagcacgaat ctcttgaatt cgtgcttgtt tgttcccggg      60

<210> SEQ ID NO 47
<211> LENGTH: 60
<212> TYPE: DNA
<213> ORGANISM: Artificial Sequence
<220> FEATURE:
<223> OTHER INFORMATION: nAchR \5 SC siRNA1-F primer
<220> FEATURE:
<221> NAME/KEY: misc_feature
<222> LOCATION: (1)..(60)
<223> OTHER INFORMATION: shRNA

<400> SEQUENCE: 47 gatccctag acgcgttttc tctcgtttca agagaacgag agaaaacgcg tctatttta       60

<210> SEQ ID NO 48
<211> LENGTH: 60
<212> TYPE: DNA
<213> ORGANISM: Artificial Sequence
<220> FEATURE:
<223> OTHER INFORMATION: nAchR \5 SC siRNA1-R primer
<220> FEATURE:
<221> NAME/KEY: misc_feature
<222> LOCATION: (1)..(60)
<223> OTHER INFORMATION: shRNA

<400> SEQUENCE: 48
agcttaaaaa tagacgcgtt ttctctcgtt ctcttgaaac gagagaaaac gcgtctaggg      60

<210> SEQ ID NO 49
<211> LENGTH: 60
<212> TYPE: DNA
<213> ORGANISM: Artificial Sequence
<220> FEATURE:
<223> OTHER INFORMATION: nAchR \5 SC siRNA2-F primer
<220> FEATURE:
<221> NAME/KEY: misc_feature
<222> LOCATION: (1)..(60)
<223> OTHER INFORMATION: shRNA

<400> SEQUENCE: 49 gatcccata cacgtatgcc tccttcttca agagagaagg aggcatacgt gtatttttta      60

<210> SEQ ID NO 50
<211> LENGTH: 60
<212> TYPE: DNA
<213> ORGANISM: Artificial Sequence
<220> FEATURE:
<223> OTHER INFORMATION: nAchR \5 SC siRNA2-R primer
<220> FEATURE:
<221> NAME/KEY: misc_feature
<222> LOCATION: (1)..(60)
```

-continued

<223> OTHER INFORMATION: shRNA

<400> SEQUENCE: 50
agcttaaaaa atacacgtat gcctccttct ctcttgaaga aggaggcata cgtgtatggg    60

<210> SEQ ID NO 51
<211> LENGTH: 18
<212> TYPE: DNA
<213> ORGANISM: Artificial Sequence
<220> FEATURE:
<223> OTHER INFORMATION: Human nAchR \9-F primer
<220> FEATURE:
<221> NAME/KEY: misc_feature
<222> LOCATION: (1)..(18)
<223> OTHER INFORMATION: Synthetic oligonucleotide for real-time PCR

<400> SEQUENCE: 51
tacatcgcca agtgcctc                                                   18

<210> SEQ ID NO 52
<211> LENGTH: 20
<212> TYPE: DNA
<213> ORGANISM: Artificial Sequence
<220> FEATURE:
<223> OTHER INFORMATION: Human nAchR \9-R primer
<220> FEATURE:
<221> NAME/KEY: misc_feature
<222> LOCATION: (1)..(20)
<223> OTHER INFORMATION: Synthetic oligonucleotide for real-time PCR

<400> SEQUENCE: 52
tgtgactaat ccgctcttgc                                                 20

<210> SEQ ID NO 53
<211> LENGTH: 23
<212> TYPE: DNA
<213> ORGANISM: Artificial Sequence
<220> FEATURE:
<223> OTHER INFORMATION: Human GUS-F primer
<220> FEATURE:
<221> NAME/KEY: misc_feature
<222> LOCATION: (1)..(23)
<223> OTHER INFORMATION: Synthetic oligonucleotide for real-time PCR

<400> SEQUENCE: 53
agtgttccct gctagaatag atg                                             23

<210> SEQ ID NO 54
<211> LENGTH: 20
<212> TYPE: DNA
<213> ORGANISM: Artificial Sequence
<220> FEATURE:
<223> OTHER INFORMATION: Human GUS-R primer
<220> FEATURE:
<221> NAME/KEY: misc_feature
<222> LOCATION: (1)..(20)
<223> OTHER INFORMATION: Synthetic oligonucleotide for real-time PCR

<400> SEQUENCE: 54
aaacagcccg tttacttgag                                                 20

<210> SEQ ID NO 55
<211> LENGTH: 31
<212> TYPE: DNA
<213> ORGANISM: Artificial Sequence
<220> FEATURE:
<223> OTHER INFORMATION: nAchR \9 Tet-off-F primer
<220> FEATURE:
<221> NAME/KEY: misc_feature
<222> LOCATION: (1)..(31)

```
<223> OTHER INFORMATION: Synthetic oligonucleotide for cloning

<400> SEQUENCE: 55
gttgaattct atgaactggt cccattcctg c                                31

<210> SEQ ID NO 56
<211> LENGTH: 30
<212> TYPE: DNA
<213> ORGANISM: Artificial Sequence
<220> FEATURE:
<223> OTHER INFORMATION: nAchR \9 Tet-off-R primer
<220> FEATURE:
<221> NAME/KEY: misc_feature
<222> LOCATION: (1)..(30)
<223> OTHER INFORMATION: Synthetic oligonucleotide for cloning

<400> SEQUENCE: 56
gcgtctagac taatccgctc ttgctatgat                                  30

<210> SEQ ID NO 57
<211> LENGTH: 30
<212> TYPE: DNA
<213> ORGANISM: Artificial Sequence
<220> FEATURE:
<223> OTHER INFORMATION: forward primer
<220> FEATURE:
<221> NAME/KEY: misc_feature
<222> LOCATION: (1)..(30)

<400> SEQUENCE: 57
gttgaattca tgaactggtc ccattcctgc                                  30

<210> SEQ ID NO 58
<211> LENGTH: 30
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<222> LOCATION: (1)..(30)

<400> SEQUENCE: 58
gatggatccc taatccgctc ttgctatgat                                  30
```

SMALL INTERFERING RNAS AND METHODS FOR PREVENTION, INHIBITION AND/OR TREATMENT OF MALIGNANT PROGRESSION OF BREAST CANCER

FIELD OF THE INVENTION

The invention relates to small interfering RNAs (siRNAs) for inhibiting expression of α9-nAChR so as to inhibit breast cancer, methods to prevent/inhibit/treat malignant progression of nicotine-derived-compound-induced breast cancer (breast cancer induced by nicotine derived compounds) and method of determining malignant level of such breast cancer.

BACKGROUND OF THE INVENTION

Breast cancer is among the most common malignant tumors and is the leading cause of death from cancer among women. The incidence of breast cancer has been steadily increasing over the past fifty years. Worldwide, it is estimated that more than one million women are diagnosed with breast cancer every year, and more than 410,000 will die from the disease. Various risk factors can increase a woman's chance of developing breast cancer, such as age, personal and family history of breast cancer, exposure to radiation, social and economical class, pregnancy, menarche, menopause, and age of first pregnancy. Tobacco, one of the most widely examined environmental factors, contains human carcinogens that contribute to a woman's risk of developing breast cancer. Epidemiological cohort studies with large numbers of participants in the United States and Japan have indicated that breast cancer risk is associated with active and passive smoking.

Previous studies using a soft agar transforming assay and a mouse xenograft model demonstrated that noncancerous MCF-10A human breast epithelial cells can become neoplastically transformed by exposure to either a cigarette smoke condensate or the tobacco-specific carcinogen 4-(methylnitrosamino)-1-(3-pyridyl)-1-butanone (NNK) (Mei J, Hu H, McEntee M, et al. *Breast Cancer Res Treat* 2003; 79(1):95-105; Siriwardhana N, Choudhary S, Wang H C. *Breast Cancer Res Treat* 2008; 109(3):427-41). In vivo studies have demonstrated that nicotine promotes the growth of solid tumors, suggesting that nicotine might contribute to the progression of cell proliferation, invasion, and angiogenesis in tumors.

Human neuronal tissues have been reported to have the most abundant expression of the nicotinic acetylcholine receptor (nAChR) subunit. These nAChRs occur as heteropentamers comprised of a combination of α subunits (α1-α6) and β subunits (β2-β4) or as homopentamers derived from subunits α7-α10 symmetrically arranged around a central ion pore. However, reverse transcription-polymerase chain reaction (RT-PCR), immunoblotting, and flow cytometry analyses have provided considerable evidence for the expression of nAChRs in nonneuronal cells outside of the nervous system, including bronchial epithelium membranes and endothelial cells (West K A, Brognard J, Clark A S, et al. *J Clin Invest* 2003; 111(1):81-90; Egleton R D, Brown K C, Dasgupta P. *Trends Pharmacol Sci* 2008; 29(3):151-8.) The physiological ligand of nAChRs is acetylcholine; however, tobacco components such as nicotine and NNK are also known to be high affinity nAChR agonists (Schuller H M. *Life Sci* 2007; 80(24-25):2274-80; Schuller H M, Orloff M. *Biochem Pharmacol* 1998; 55(9):1377-84.) Cigarette smoking is known to be a prominent risk factor for lung, colon, and bladder cancers, all of which express α7 as a major nAChR, as well as breast cancers, which express α9-nAChR, suggesting that agents such as nicotine and NNK may function in a receptor-dependent manner (Wong H P, Yu L, Lam E K, et al. *Toxicol Sci* 2007; 97(2):279-87; West K A, Brognard J, Clark A S, et al. *J Clin Invest* 2003; 111(1):81-90; Wong H P, Yu L, Lam E K, et al. *Toxicol Appl Pharmacol* 2007; 221(3):261-7; Chen R J, Ho Y S, Guo H R, et al. *Toxicol Sci* 2008; 104(2):283-93.) Yung-Leun Shih et al. indicates that nicotine significantly increased α9-nAChR mRNA and protein expression levels in human breast cancer cells (Yung-Leun Shih et al., *J. Agric. Food. Chem.* 2010, 58, 235-241). However, the reference is silent on the relationship of expression of α9-nAChR and tumorigenesis of breast cancer. Ching-Shyang Chen et al. elucidate whether Nic/nicotinic acetylcholine receptor (nAChR) binding could affect cyclin D3 expression in human breast cancer cells and the carcinogenic role of cyclin D3. The cyclin D3 expression cannot suggest the overexpression and activation of α9-nAChR per se.

Unlike the nAChRs that are expressed in normal neuronal cells, most of the nAChRs present in cancer cell lines have not been functionally characterized (Egleton R D, Brown K C, Dasgupta P. *Trends Pharmacol Sci* 2008; 29(3):151-8.) In cancer cells, nAChRs could also play a role in the acquisition of chemotherapy drug resistance. Nicotine has been shown to protect cells against apoptosis, so nAChR antagonists could potentially be used in combination with established chemotherapeutic drugs to enhance therapeutic response to chemotherapy.

The ability to identify breast cancer patients with more aggressive diseases is crucial to accurate prognosis and planning for adequate treatment. Identifying the alterations in gene expression which are associated with malignant tumors, including those involved in tumor progression, is clearly a prerequisite not only for a full understanding of cancer, but also to develop new rational therapies against cancer. Unfortunately, there is presently no sufficiently accurate method of determining malignant progression and metastatic potential of breast cancer.

SUMMARY OF THE INVENTION

The invention provides an siRNA molecule for suppressing expression of α9-nAChR gene via RNA interference (RNAi), which comprises: a sense strand having at least the sequence of SEQ ID NO: 1 or SEQ ID NO: 3 or a complementary sequence thereof having sufficient complementarity to an RNA of said α9-nAChR gene for the siRNA molecule to direct cleavage of said RNA via RNA interference.

The invention also provides a method of preventing and/or inhibiting and/or treating malignant progression of nicotine-derived-compound-induced breast cancer in a subject, comprising administering to said subject an α9-nAChR inhibitor in an amount effective to reduce α9-nAChR expression, thereby treating preventing and/or inhibiting and/or treating malignant progression of such breast cancer.

The invention further provides a method of diagnosing malignant level of nicotine-derived-compound-induced breast cancer, comprising determining α9-nAChR expression level in a sample from the breast cells or tissue of a subject; wherein a more than two fold elevated level indicates a likelihood that the subject has breast cancer with differentiation over stage 1.

DETAILED DESCRIPTION OF THE INVENTION

Figure 1:
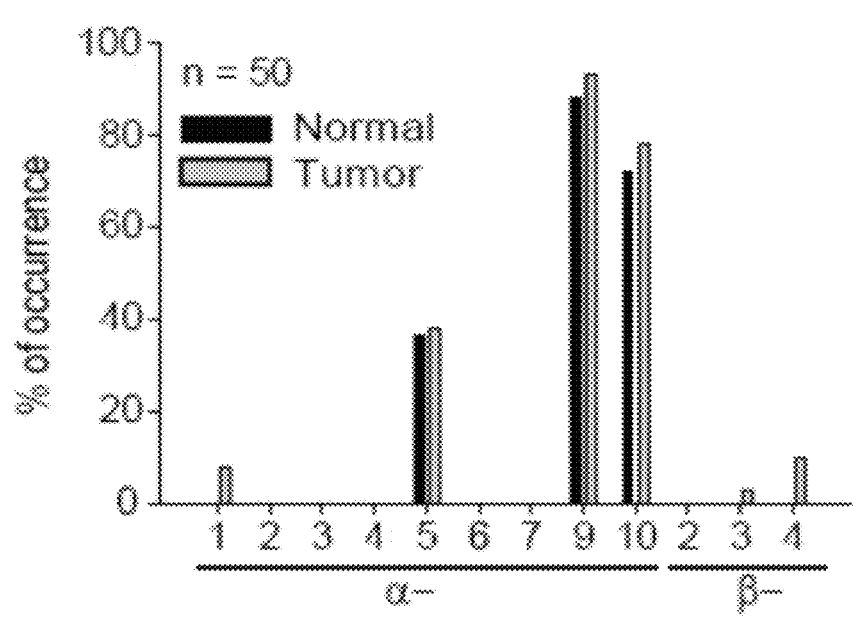
FIG. 1 shows the role of nicotine-α9-nicotinic acetylcholine receptor (nAChR) binding in human breast cancer cell proliferation. A) Detection of nAChR subunits by reverse transcription-polymerase chain reaction (RT-PCR) in normal and cancerous human breast cell lines. MCF-7, MDA-MB-231, AU-565, MDA-MB-453, and BT-483 are transformed human breast cancer cells; MCF-10A and HBL-100 are considered normal human breast cells. The expression profiles of nAChR subunits in human SAEC (small airway epithelial), NHBE (normal human bronchial epithelial), and H157 (lung cancer) cells were also examined as described previously (West K A, Brognard J, Clark A S, et al. *J Clin Invest* 2003; 111(1):81-90). B) Relative mRNA expression of different nAChR subunits in normal and tumor human breast tissues isolated from 50 breast cancer patients. The cDNA was used for RT-PCR analysis and the experiment was repeated twice. Percent of occurrence is shown. C) Expression of the α5 and α9 nAChR subunits in stable MDA-MB-231 cell lines that express α9-nAChR (Si α9), α5-nAChR (Si α5), or scrambled (Sc) short interfering RNAs (siRNAs). Cell lines in which expression of the α5- or α9-nAChRs was specifically reduced were generated by transfection and G418 (4 mg/mL) selection. Levels of α5 and α9 mRNAs were determined by RT-PCR, and levels of the α5 and α9 proteins by western blotting (WB). In each case, glyceraldehyde 3-phosphate dehydrogenase (GADPH) expression served as a control. D) Cell proliferation in Si α5, Sc, and parental MDA-MB-231 cells treated with dimethylsulfoxide DMSO vs nicotine, and in cells treated with DMSO vs the nicotine metabolite, 4-(methylnitrosamino)-1-(3-pyridyl)-1-butanone (NNK). Parental MDA-MB-231 cells (231) and 231 cells stably transformed the Si α5-, Sc-, or Si α9-siRNAs were treated with either nicotine (10 μM), NNK (1 μM), or vehicle alone in the absence of continued G418 selection afterwards. Cells from each group were treated with G418 to confirm successful expression of pSUPER siRNA plasmids. Cell proliferation was measured by the 3-(4,5-dimethylthiazol-2-yl)-2,5-diphenyltetrazolium (MTT) assay, in which a greater number of cells was reflected by an increased $OD_{540\,nm}$ at the indicated time points. The experiment was repeated four times with duplicate samples. Data points represent the mean; error bars indicate 95% confidence intervals. The data were analyzed by nonparametric two-sided tests (Kruskal-Wallis and Mann-Whitney tests). On day 11 in MDA-MB-231, Sc, or Si α5 cells, the mean $OD_{540\,nm}$ of DMSO-treated cells was statistically significantly different than that for nicotine- and NNK-treated cells (P=0.009 for all comparisons). E) Confocal microscopy of α9-nAChR expression in human breast cancer (MCF-7) cells. Immunofluorescence with a fluorescein isothiocyate-conjugated secondary antibody was used to detect the α9-nAChR, whereas a rhodamine-conjugated fluorescent antibody was used for caveolin-1 labeling. Localization of α9-nAChR (left, green), the membrane protein caveolin-1 (middle, red), and the merged image (right, yellow) are shown. Scale bar=25 μm. F) Dose-dependent binding of [$^3$H]-nicotine to the endogenous α9-nAChR receptor in human breast cancer MDA-MB-231 cells (left panel) and time-dependent [$^3$H]-nicotine binding in parental MDA-MB-231 cells (231), or in 231 cells stably transformed with α9-nAChR siRNA (Si α9) or scrambled control (Sc) siRNA (right panel). The experiment was repeated four times with duplicate samples. Data points represent the mean; error bars indicate the 95% confidence intervals. The data were analyzed by two-sided nonparametric tests (Kruskal Wallis and Mann-Whitney test): Si α9-expressing cells bound statistically significantly less [$^3$H]-nicotine than parental (231) or control (Sc) cells (for both comparisons, P=0.009). G) Analysis of α9-nicotinic acetylcholine receptor (α9-nAChR) expression in human breast carcinoma tissues. Determination of α9-nAChR mRNA levels using reverse transcription-polymerase chain reaction (RT-PCR). Both α9-nAChR and β-glucuronidase (GUS) transcripts were detected as single bands (403 and 165 base pairs, respectively) in both tumor and adjacent normal tissues. PCR was performed for 30 cycles. The agarose gel image showed 50 randomly-chosen and representative patients.
Figure 1:
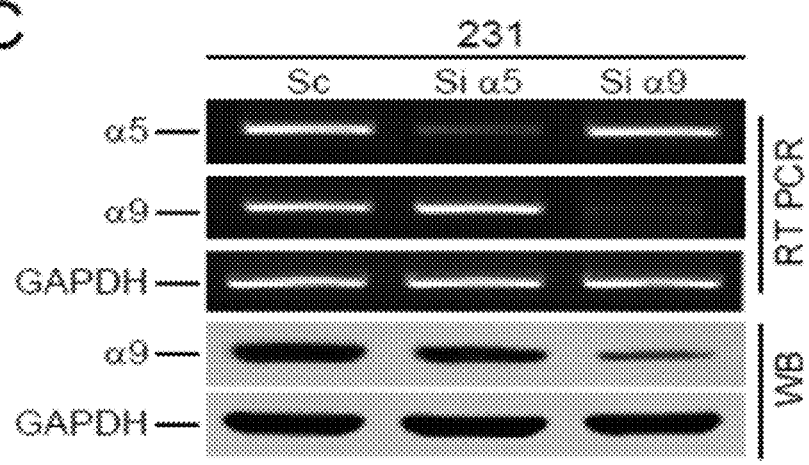
Figure 1:
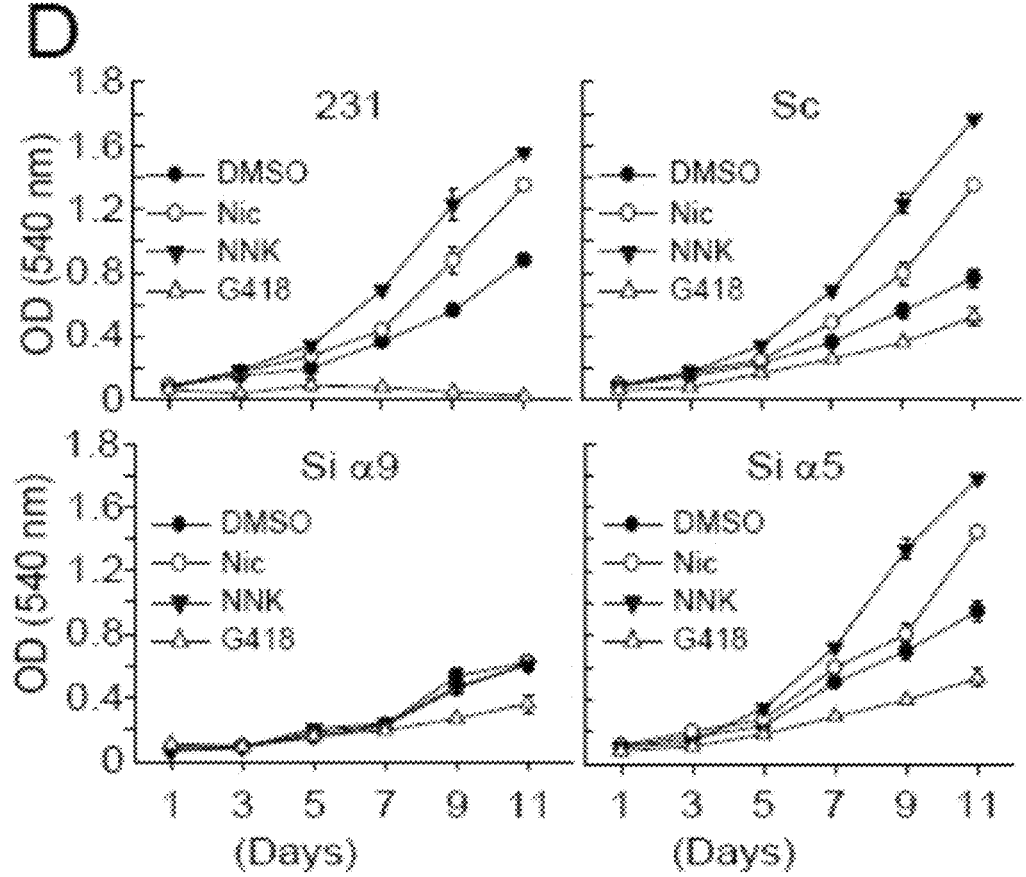
Figure 1:
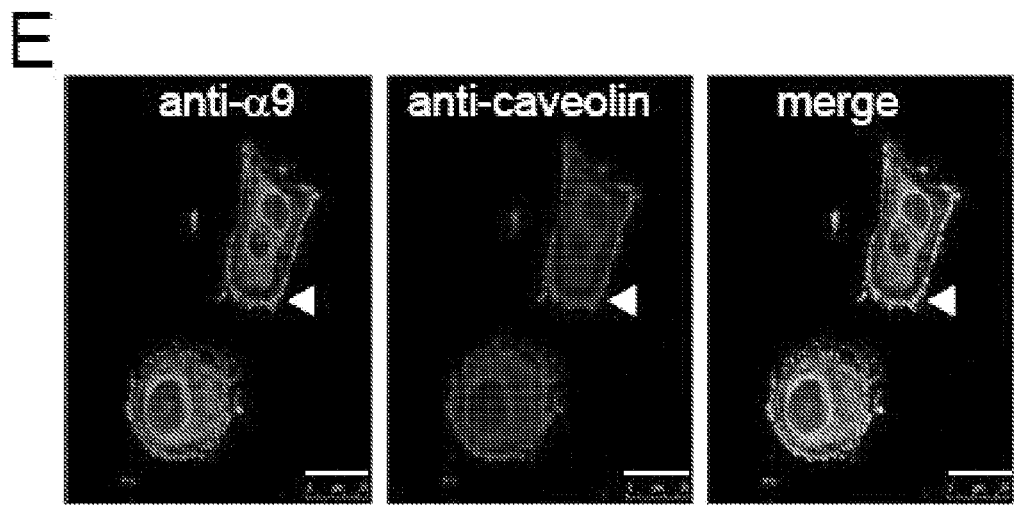
Figure 1:
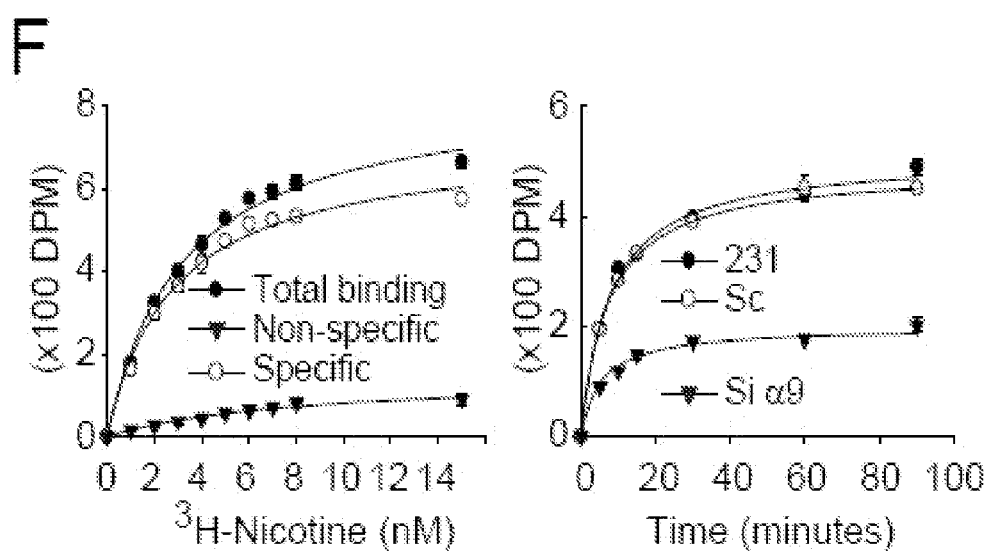
Figure 1:
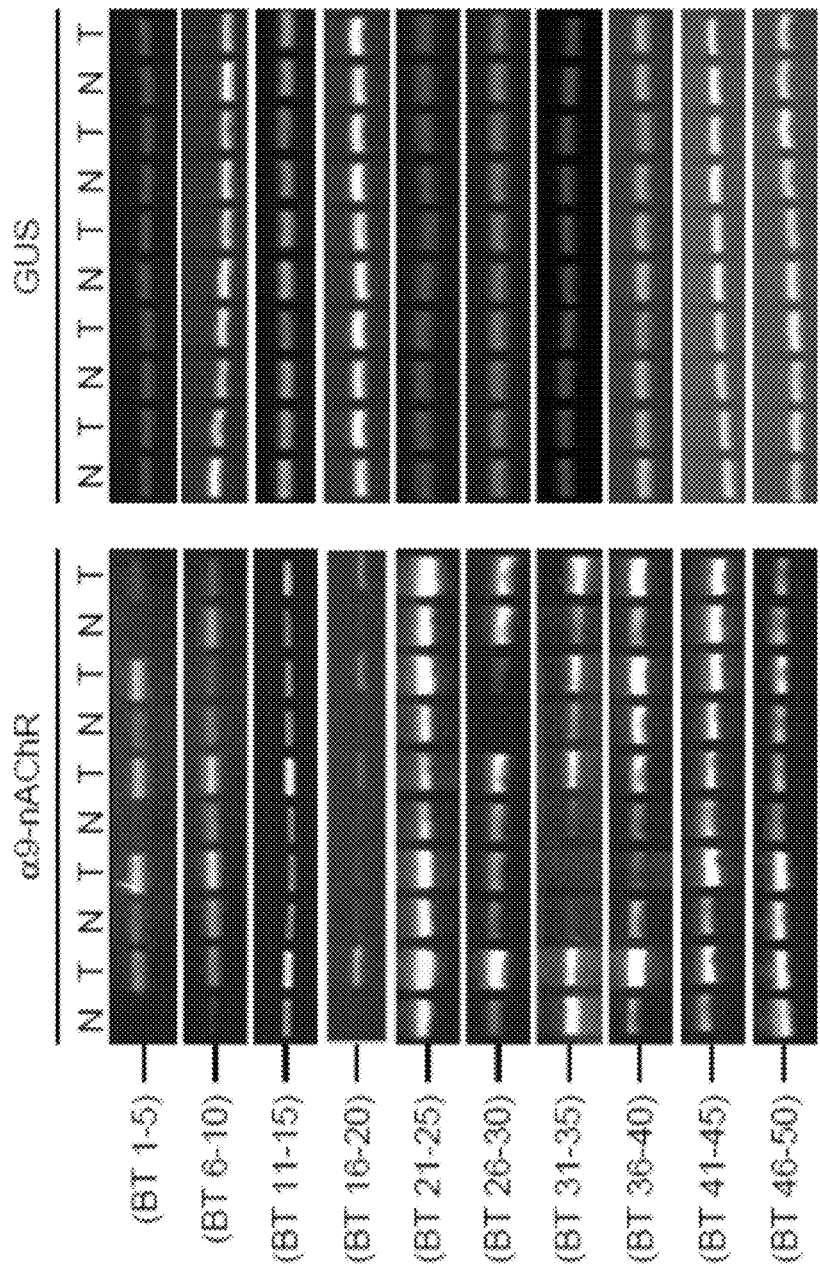

The invention unexpectedly discovers that overexpression and activation of α9-nAChR are associated with tumorigenesis of breast cancer and create a number of small interfering RNAs to inhibit the expression of α9-nAChR so as to inhibit breast cancer. Furthermore, the invention surprisingly finds that the expression of α9-nAChR is relevant to malignant progression of breast cancer and transformation of breast cancer cells. Particularly, the α9-nAChR expression level increases in a differentiation stage dependent manner On the basis of these discoveries, the expression of α9-nAChR can be used to determinate level of malignancy of breast cancer (in particular, nicotine-derived-compound-induced breast cancer).

DEFINITIONS

The use of the word "a" or "an" when used in conjunction with the term "comprising" in the claims and/or the specification may mean "one," but is also consistent with the meaning of "one or more," "at least one," and "one or more than one."

The term "overexpression" refers to the level of expression in cells or organisms that exceeds levels of expression in normal cells or organisms.

The term "target" is used in a variety of different forms throughout this document and is defined by the context in which it is used. "Target mRNA" refers to a messenger RNA to which a given siRNA can be directed against. "Target sequence" and "target site" refer to a sequence within the mRNA to which the sense strand of an siRNA shows varying degrees of homology and the antisense strand exhibits varying degrees of complementarity. The phrase "siRNA target" can refer to the gene, mRNA, or protein against which an siRNA is directed. Similarly, "target silencing" can refer to the state of a gene, or the corresponding mRNA or protein.

The phrase "gene silencing" refers to a process by which the expression of a specific gene product is lessened or attenuated. Gene silencing can take place by a variety of pathways. Unless specified otherwise, as used herein, gene silencing refers to decreases in gene product expression that result from RNA interference (RNAi), a defined, though partially characterized pathway whereby small interfering RNA (siRNA) act in concert with host proteins (e.g., the RNA induced silencing complex, RISC) to degrade messenger RNA (mRNA) in a sequence-dependent fashion. The level of gene silencing can be measured by a variety of means, including, but not limited to, measurement of transcript levels by Northern Blot Analysis, B-DNA techniques, transcription-sensitive reporter constructs, expression profiling (e.g., DNA chips), and related technologies. Alternatively, the level of silencing can be measured by assessing the level of the protein encoded by a specific gene. This can be accomplished by performing a number of studies, including Western Analysis, measuring the levels of expression of a reporter protein that has, for example, fluorescent properties (e.g., GFP) or enzymatic activity (e.g., alkaline phosphatases), or several other procedures.

The phrase "inhibiting expression of a target gene" refers to the ability of an siRNA molecule of the present invention to silence, reduce, or inhibit expression of a target gene (e.g., α9-nAChR gene). To examine the extent of gene silencing, a test sample (e.g., a biological sample from an organism of interest expressing the target gene or a sample of cells in culture expressing the target gene) is contacted with an siRNA that silences, reduces, or inhibits expression of the target gene. Expression of the target gene in the test sample is compared to expression of the target gene in a control sample that is not contacted with the siRNA or that is contacted with scrambled sequences of siRNA. Control samples are assigned a value of 100%. Silencing, inhibition, or reduction of expression of a target gene is achieved when the value of the test sample relative to the control sample is about 95%, 90%, 85%, 80%, 75%, 70%, 65%, 60%, 55%, 50%, 45%, 40%, 35%, 30%, 25%, 20%, or 10%. Suitable assays include, for example, examination of protein or mRNA levels using techniques known to those skilled in the art, such as dot blots, Northern blots, in situ hybridization, ELISA, immunoprecipitation, enzyme function, as well as phenotypic assays known to those of skill in the art.

The terms "short interfering nucleic acid," "siNA," "short interfering RNA," "siRNA," "short interfering nucleic acid molecule," "short interfering oligonucleotide molecule," or "chemically-modified short interfering nucleic acid molecule" as used herein refer to any nucleic acid molecule capable of inhibiting or down regulating the expression of a target gene. These molecules can vary in length (generally between 18-80 base pairs) and contain varying degrees of complementarity to their target mRNA in the antisense strand. Some but not all siRNA have unpaired overhanging bases on the 5' or 3' end of the sense strand and/or the antisense strand. The term "siRNA" includes duplexes of two separate strands, as well as single strands that can form hairpin structures comprising a duplex region.

The term "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated. Perfect complementarity or 100% complementarity refers to the situation in which each nucleotide unit of one polynucleotide strand can hydrogen bond with a nucleotide unit of a second polynucleotide strand. Less than perfect complementarity refers to the situation in which some but not all nucleotide units of two strands can hydrogen bond with each other. For example, for two 20-mers, if only two base pairs on each strand can hydrogen bond with each other, the polynucleotide strands exhibit 10% complementarity. In the same example, if 18 base pairs on each strand can hydrogen bond with each other, the polynucleotide strands exhibit 90% complementarity.

The phrase "duplex region" refers to the region in two complementary or substantially complementary polynucleotides that form base pairs with one another, either by Watson-Crick base pairing or any other manner that allows for a stabilized duplex between polynucleotide strands that are complementary or substantially complementary.

The term "inhibitor" as used herein refers to a compound, molecule, or agent that inhibits a biological activity. The term "α9-nicotinic acetyl choline receptor inhibitor" refers to inhibitors that substantially inhibit expression or activity of α9-nicotinic acetylcholine receptor (α9-nAChR) and provide a pharmacological effect. The term "α9-nAChR inhibitor" encompasses naturally-occurring compounds, endogenous ligands, and synthetically produced compounds, and pharmaceutically acceptable salts of the foregoing. Examples of α9-nAChR inhibitor molecules include, but are not limited to, peptides, small molecules, antibodies, antisense nucleic acids, siRNA nucleic acids, and other binding agents.

The term "effective amount" as used herein when referring to an inhibitor means the amount or dosage of that inhibitor that is required to induce a desired effect. In some embodiments, an effective dose refers to an amount that is required to inhibit expression of α9-nAChR.

The term "sample" as used herein refers to a biological sample, such as, for example, tissue or fluid isolated from a subject (including without limitation plasma, serum, cerebrospinal fluid, lymph, tears, saliva and tissue sections) or from in vitro cell culture constituents.

The term "malignant" refers to a serious form of cancer that may affect the cancerous cells only or may spread (metastasize) through the blood or lymph systems to organs and bones.

The term "treat," "treatment" or "treating" means reducing the frequency, extent, severity and/or duration with which symptoms of breast cancer are experienced by a patient.

The term "prevent," "prevention" or "preventing" means inhibition or the averting of symptoms associated with breast cancer.

Short Interfering RNAs (siRNAs) of the Invention

The invention provides an siRNA molecule for suppressing expression of α9-nAChR gene via RNA interference (RNAi), which comprises: a sense strand having at least the sequence of SEQ ID NO: 1 or SEQ ID NO: 3 or a complementary sequence thereof having sufficient complementarity to an RNA of said α9-nAChR gene for the siRNA molecule to direct cleavage of said RNA via RNA interference. In one embodiment of the invention, the siRNA molecule is a sequence further comprising a hairpin loop region and a sequence complementary to SEQ ID NO: 1 or SEQ ID NO: 3, or a complementary sequence thereof having sufficient complementarity to an RNA of said α9-nAChR gene for the siRNA molecule to direct cleavage of said RNA via RNA interference. Preferably, the siRNA molecule comprises a sequence as shown in SEQ ID NO: 5 and 7. According to the invention, when the siRNA molecule has a hairpin loop region, it can be a linear form or form a hairpin turn and both linear and hairpin forms can be used to silence gene expression via RNA interference. Moreover, the hairpin loop region is not an essential element of the siRNA molecule of the invention. Even if the siRNA molecule has no hairpin loop, it still can be used to silence gene expression via RNA interference. Any hairpin loop regions known in the art can be used in the invention and they can vary in length. In some embodiments the loop is 5, 6, 7, 8, 9, 10, 11, 12 or 13 nucleotides in length. Preferably, the hairpin loop region is of the sequence TTCAAGAGA (SEQ ID nO:9) or TCTCTTGAA (SEQ ID NO:10).

In another embodiment of the invention, the siRNA molecule can be a sequence complementary to the above sequences having the hairpin loop region. Preferably, these sequences are of the sequences as shown in SEQ ID NO: 6 and 8.

According to the invention, the complementarity of a sequence has 70%, 80%, 90%, or 100% complementary to its corresponding sequence. In a preferred embodiment, the sequences perfectly complementary to SEQ ID NO: 1 and SEQ ID NO: 3 are SEQ ID NO: 2 and SEQ ID NO: 4, respectively. In another embodiment, the sequences perfectly complementary to SEQ ID NO: 5 and SEQ ID NO: 7 are SEQ ID NO: 6 and SEQ ID NO: 8, respectively.

According to the invention, the siRNA molecule is about 19 to about 80 nucleotides in length. Preferably, the siRNA molecule is about 19 to about 70, about 19 to about 60, about 19 to about 40 or about 19 to about 30 nucleotides in length. I According to the invention, the sequences of SEQ ID NOs: 1 to 8 are as follows:

```
                                               SEQ ID NO: 1
TGTGATCTCCTATGGCTGC

SEQ ID NO: 2
ACACTAGAGGATACCGACG

SEQ ID NO: 3
AAAGCAGCCAGGAACAAAG

SEQ ID NO: 4
TTTCGTCGGTCCTTGTTTC

SEQ ID NO: 5
TGTGATCTCCTATGGCTGCTTCAAGAGAGCAGCCATAGGAGATCACA

SEQ ID NO: 6
ACACTAGAGGATACCGACGAAGTTCTCTCGTCGGTATCCTCTAGTGT

SEQ ID NO: 7
AAAGCAGCCAGGAACAAAGTTCAAGAGACTTTGTTCCTGGCTGCTTT

SEQ ID NO: 8
TTTCGTCGGTCCTTGTTTCAAGTTCTCTGAAACAAGGACCGACGAAA
```

In one embodiment of the invention, the siRNA molecule further have at least one overhang region. Preferably, each overhang region contains six or fewer nucleotides. The overhang region is not an essential element of the siRNA molecule of the invention. According to the invention, the overhang region is a non-complementary region in the sense strand or antisense strand. An overhang is a stretch of unpaired nucleotides in the end of an siRNA molecule. These unpaired nucleotides can be in either strand, creating either 3' or 5' overhangs. Preferably, the siRNA sequence having overhang region is of the sequence as shown in SEQ ID NO: 11, SEQ ID NO: 12, SEQ ID NO:13 or SEQ ID NO: 14.

The sequences of SEQ ID NOs: 11, 12, 13 and 14 are as follows:

(SEQ ID NO: 11)
GATCCCCTGTGATCTCCTATGGCTGCTTCAAGAGAGCAGCCATAGGA

GATCACATTTTTA;

(SEQ ID NO: 12)
AGCTTAAAAATGTGATCTCCTATGGCTGCTCTCTTGAAGCAGCCATA

GGAGATCACAGGG (SEQ ID NO: 13)
GATCCCCAAAGCAGCCAGGAACAAAGTTCAAGAGACTTTGTTCCTGG

CTGCTTTTTTTA (SEQ ID NO: 14)
AGCTTAAAAAAAAGCAGCCAGGAACAAAGTCTCTTGAACTTTGTTCC

TGGCTGCTTTGGG

An siRNA molecule of the invention can be unmodified or chemically modified. An siRNA of the instant invention can be chemically synthesized, expressed from a vector or enzymatically synthesized. The present invention also features various chemically modified synthetic short interfering nucleic acid (siRNA) molecules capable of inhibiting α9-nAChR gene expression or activity in cells by RNA interference (RNAi). The use of chemically modified siRNA improves various properties of native siRNA molecules through increased resistance to nuclease degradation in vivo and/or through improved cellular uptake. Further, contrary to earlier published studies, siRNA having multiple chemical modifications retains its RNAi activity. The siRNA molecules of the present invention provide useful reagents and methods for a variety of therapeutic, diagnostic, target validation, genomic discovery, genetic engineering, and pharmacogenomic applications.

In some embodiments, the siRNA molecule described herein further comprises a carrier system, for example, to deliver the siRNA molecule into a cell of a mammal. Non-limiting examples of carrier systems suitable for use in the present invention include nucleic acid-lipid particles, liposomes, micelles, virosomes, nucleic acid complexes, and mixtures thereof. In certain instances, the siRNA molecule is complexed with a lipid such as a cationic lipid to form a lipoplex. In certain other instances, the siRNA molecule is complexed with a polymer such as a cationic polymer (e.g., polyethylenimine (PEI)) to form a polyplex. The siRNA molecule may also be complexed with cyclodextrin or a polymer thereof. Preferably, the siRNA molecule is encapsulated in a nucleic acid-lipid particle.

The present invention also provides a pharmaceutical composition comprising an siRNA molecule described herein and a pharmaceutically acceptable carrier.

Methods of Preventing and/or Inhibiting and/or Treating Malignant Progression of Nicotine-Derived-Compound-Induced Breast Cancer In another aspect, the invention provides a method of preventing and/or inhibiting and/or treating malignant progression of nicotine-derived-compound-induced breast cancer, comprising administering to a subject an α9-nAChR inhibitor in an amount effective to reduce α9-nAChR expression, thereby treating preventing and/or inhibiting and/or treating malignant progression of the breast cancer.

It is known in the art that nicotine is not a carcinogen but nitrosation of nicotine gives NNN ("N'-nitrosonomicotine") by cleavage of the N—$CH_3$ bond with loss of formaldehyde or yields NNK ("4-(methyl1nitros-amino)-t-(3-pyridyl)-1-butanone" (the origin of the term NNK is "nicotine-derived nitrosaminoketone") or NNA ("4-fmethylnitrosamino)-4-{3-pyridyl)-butanal") by cleavage of either the 2'-N or 5'-N bond, respectively (*Cancer Research* 45, 935-944, March 1985, which is incorporated herein by reference in its entirety).

According to the invention, the α9-nAChR inhibitor used in the method of the invention is an agent reducing the expression or activity of α9-nAChR. Any of a variety of α9-nAChR inhibitors can be used in the methods of the present invention. Examples include, but are not limited to, siRNAs, antisense RNAs, nicotine, atropine, muscarine, strychnine, bicuculline, ICS-205.930, tropisetron, d-tubocurarine, methylycaconitine, α-bungarotoxin, PeIA, Vc1.1 (ACV1), vcla, α-ImI, α-RgIA and α-ImII—(Biochemical Pharmacology 78 (2009) pp. 693-702; Mol. Pharmacol 72:1406-1410, 2007; and PNAS 2006, Vol. 103, No. 47, pp. 17880-17884, which are incorporated herein by reference in their entirety).

The α9-nAChR inhibitor can be formulated with one or more acceptable carriers, excipients, or diluents for administration. Pharmaceutically acceptable carriers for therapeutic use are well known in the pharmaceutical art, and are described, for example, in Remington's Pharmaceutical Sciences, Gennaro, A R, ed., 20th edition, 2000: Williams and Wilkins Pa., USA, which is incorporated herein by reference for all purposes. While any known suitable carrier may be employed in a pharmaceutical formulation of this invention, the type of carrier will vary depending on the mode of administration and whether a sustained release is desired. Routes of delivery may include oral, inhaled, buccal, parenteral, and transdermal routes, as well as novel delivery systems such as the protective liposomes for oral delivery of peptides.

For oral administration, a carrier preferably comprises carbohydrate or polypeptide fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and polypeptides such as gelatin and collagen. If desired, disintegrating or solubilizing agents may be added, such as the cross-linked polyvinyl pyrrolidone, agar, alginic acid, or a salt thereof, such as sodium alginate. If desirable, the drug can be delivered in nanocapsules that would protect against proteolysis by proteases. Such carriers enable the compositions herein to be formulated as tablets, pills, dragees, capsules, liquids, gels, syrups, slurries, suspensions, and the like, for ingestion by the patient. Pharmaceutical preparations for oral use can be obtained through a combination of active compounds with solid excipient and processing the mixture of granules, after adding suitable auxiliaries, if desired, to obtain tablets or dragee cores. As the composition may be peptide and nucleic acid, such peptides and nucleic acids are preferably put into a liposomal formulation to avoid degradation.

Preferably the pharmaceutical formulations herein are administrated by intravenous injection or by local application (e.g., topical or subdermal).

Formulations for topical administration can use a carrier that is a solution, emulsion, and ointment or gel base. The base, for example, may comprise one or more of the following: petrolatum, lanolin, PEGs, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

Any of the α9-nAChR inhibitors used in the method of the invention may be co-formulated or co-administered with a second anti-cancer agent. The second anti-cancer agent can be any anti-cancer drug known in the art.

Normal dosage amounts of the α9-nAChR inhibitors used in the method of the invention may vary from 10 mg/kg/day to 500 mg/kg/day, depending upon the route of administration. Preferably, the dosage amount is 10-450, 10-400, 10-300, 10-200, 10-100, 50-400, 50-400, 50-350, 50-300, 50-200, 100-400, 100-300 or 100-200 mg/kg/day. Guidance as to particular dosages and methods of delivery is provided in the literature and generally available to practitioners in the art. Those skilled in the art will employ different formulations for nucleotides than for polypeptides or their inhibitors. Similarly, delivery of polynucleotides or polypeptides will be specific to particular cells, cell types, organism being treated, conditions, locations, etc.

The invention also provides a method of selecting a compound for preventing and/or inhibiting and/or treating malignant progression of nicotine-derived-compound-induced breast cancer, comprising contacting the compound with a cell of overexpressing α9-nAChR, wherein the compound is able to prevent and/or inhibit and/or treat malignant progression if it can reduce the expression of α9-nAChR.

Methods and Kits of Diagnosing Malignant Level of Nicotine-derived-compound-induced Breast Cancer In a further aspect, the invention provides a method of diagnosing malignant level of nicotine-derived-compound-induced breast cancer, comprising determining α9-nAChR expression level in a sample from the breast cells or tissue of a subject; wherein an elevated level more than two fold indicates a likelihood that the subject has the breast cancer with differentiation over stage 1. Preferably, elevated level more than ten fold indicates a likelihood that the subject has the breast cancer with differentiation over stage 2 and elevated level more than thirty fold indicates a likelihood that the subject has the breast cancer with differentiation over stage 3.

The invention also provides a diagnostic kit containing probes or primers for measuring the α9-nAChR expression level in a sample. According to the invention, the α9-nAChR mRNA expression level increases in a differentiation stage-dependent manner. According to the invention, the sample can be tissue or fluid isolated from a subject, including without limitation plasma, serum, cerebrospinal fluid, lymph, tears, saliva and tissue sections. For example, circulating tumor cells or metastatic cells may exist in body fluids.

In one embodiment of the diagnosis method of the present invention, an RNA sample is first prepared from a subject. Subsequently, the level of RNA encoding the protein of the present invention contained in the RNA sample is measured. Then, the measured RNA level is compared with that of a control. In another embodiment of the detection method of the present invention, a protein sample is first prepared from cells or tissue of a subject. The level of the protein of the present invention contained in the protein sample is measured. Then, the measured protein level is compared with that of a control. Examples of a method for measurement include SDS polyacrylamide electrophoresis, and methods utilizing the antibody of the invention, such as Western blotting, dot-blotting, immunoprecipitation, enzyme-linked immunosorbent assay (ELISA), and immunofluorescence.

The α9-nAChR is important for transformation of normal human breast epithelial cells induced by nicotine-derived compounds (such as nicotine). The invention found that reduction of α9-nAChR subunit expression by RNA interference in human breast cancer cells substantially inhibits tumor growth in vitro and in vivo. The α9-nAChR subunit is potentially carcinogenic in normal human breast epithelial cells in vitro and in vivo as shown by the properties of α9-nAChR-overexpressing breast cells. α9-nAChR expression is generally higher in tumor cells relative to normal cells. Levels of α9-nAChR expression in human breast tumor cells are generally increased in more advanced-stage breast cancers.

EXAMPLE

Pharmacological Assay

Cell Culture and Patient Samples

All human breast tumor samples (n=276) were obtained as specimens from anonymous donors from Taipei Medical University Hospital and Cathay General Hospital, Taipei, according to a protocol approved by the Institutional Review Board (P950012). On histological inspection, all patient samples consisted of more than 80% tumor tissue. All samples (each paired tumor vs normal tissue) were collected and categorized according to clinical information such as stage status. Human mammary gland epithelial adenocarcinomas (MCF-7, MDA-MB-231, AU-565, MDA-MB-453, and BT-483) and human normal mammary gland epithelial fibrocystic cell lines (MCF-10A and HBL-100) were purchased from the American Tissue Cell Culture collection (ATCC, Manassas, Va.). MCF-10A cells were maintained in complete MCF-10A culture medium, that is, a 1:1 mixture of Dulbecco's modified Eagle's medium (DMEM) and Ham's F12 supplemented with 100 ng/mL cholera enterotoxin, 10 μg/mL insulin, 0.5 μg/mL hydrocortisol, and 20 ng/mL epidermal growth factor (Life Technologies, Rockville, Md.). MCF-7, MDA-MB-231, HBL-100, and MDA-MB-453 cells were maintained in DMEM, whereas AU-565, and BT-483 cells were maintained in RPMI-1640.

Cell Proliferation and Viability Assays

Cell growth, proliferation, and viability were determined using the 3-(4,5-dimethylthiazol-2-yl)-2,5-diphenyltetrazolium (MTT) assay (Chou Y H, Ho Y S, Wu C C, et al. *Food Chem Toxicol* 2007; 45(8):1356-67.) Stock solutions of 10 mM nicotine and NNK (Chemsyn, Lenexa, Kans.) were prepared in dimethyl sulfoxide (DMSO). This assay was repeated four times with duplicate samples.

RNA Isolation and Real-Time Quantitative PCR

Total RNA was isolated both from human cell lines and breast tumor tissue samples acquired directly from patients (n=276) using Trizol (Invitrogen, Carlsbad, Calif.), according to the manufacturer's protocol. A portion of the samples from the original group (n=50 out of 276) were randomly-selected for the determination of nAChR expression profiles by RT-PCR. After random selection, the clinical information associated with these samples was carefully checked to ensure that there were no substantial differences between the selected and the original groups. The nAChR subunit-specific primers were synthesized as previously described (West K A, Brognard J, Clark A S, et al. *J Clin Invest* 2003; 111(1):81-90.) (see Table 1 below)

TABLE 1

| # | Primer name* | Application | Sequence |
|---|---|---|---|
| 1 | nAchR α1-F | RT-PCR | CGTCTGGTGGCAAAGCT (SEQ ID NO: 15) |
| 2 | nAchR α1-R | RT-PCR | CCGCTCTCCATGAAGTT (SEQ ID NO: 16) |
| 3 | nAchR α2-F | RT-PCR | CCGGTGGCTTCTGATGA (SEQ ID NO: 17) |
| 4 | nAchR α2-R | RT-PCR | CAGATCATTCCAGCTAGG (SEQ ID NO: 18) |
| 5 | nAchR α3-F | RT-PCR | CCATGTCTCAGCTGGTG (SEQ ID NO: 19) |
| 6 | nAchR α3-R | RT-PCR | GTCCTTGAGGTTCATGGA (SEQ ID NO: 20) |
| 7 | nAchR α4-F | RT-PCR | GAATGTCACCTCCATCCGCATC (SEQ ID NO: 21) |
| 8 | nAchR α4-R | RT-PCR | CCGGCAATTGTCCTTGACCAC (SEQ ID NO: 22) |
| 9 | nAchR α5-F | RT-PCR | TCATGTAGACAGGTACTTC (SEQ ID NO: 23) |
| 10 | nAchR α5-R | RT-PCR | ATTTGCCCATTTATAAATAA (SEQ ID NO: 24) |
| 11 | nAchR α6-F | RT-PCR | GGCCTCTGGACAAGACAA (SEQ ID NO: 25) |
| 12 | nAchR α6-R | RT-PCR | AAGATTTTCCTGTGTTCCC (SEQ ID NO: 26) |
| 13 | nAchR α7-F | RT-PCR | CACAGTGGCCCTGCAGACCGATGGTACGGA (SEQ ID NO: 27) |
| 14 | nAchR α7-R | RT-PCR | CTCAGTGGCCCTGCTGACCGATGGTACGGA (SEQ ID NO: 28) |
| 15 | nAchR α9-F | RT-PCR | GTCCAGGGTCTTGTTTGT (SEQ ID NO: 29) |
| 16 | nAchR α9-R | RT-PCR | ATCCGCTCTTGCTATGAT (SEQ ID NO: 30) |
| 17 | nAchR α10-F | RT-PCR | CTGTTCCGTGACCTCTTT (SEQ ID NO: 31) |
| 18 | nAchR α10-R | RT-PCR | GGAAGGCTGCTACATCCA (SEQ ID NO: 32) |
| 19 | nAchR β2-F | RT-PCR | CGGCTCCCTTCCAAACACA (SEQ ID NO: 33) |
| 20 | nAchR β2-R | RT-PCR | GCAATGATGGCGTGGCTGCTGCA (SEQ ID NO: 34) |
| 21 | nAchR β3-F | RT-PCR | AGAGGCTCTTTCTGCAGA (SEQ ID NO: 35) |
| 22 | nAchR β3-R | RT-PCR | GCCACATCTTCAAAGCAG (SEQ ID NO: 36) |
| 23 | nAchR β4-F | RT-PCR | CTGAAACAGGAATGGACT (SEQ ID NO: 37) |
| 24 | nAchR β4-R | RT-PCR | CCATGTCTATCTCCGTGT (SEQ ID NO: 38) |
| 25 | nAchR α9 siRNA1-F | shRNA | GATCCCCTGTGATCTCCTATGGCTGCTTCAAGAGAGCAGCCATAGGAGATCACATTTTTA (SEQ ID NO: 11) |
| 26 | nAchR α9 siRNA1-R | shRNA | AGCTTAAAAATGTGATCTCCTATGGCTGCTCTCTTGAAGCAGCCATAGGAGATCACAGGG (SEQ ID NO: 12) |

TABLE 1-continued

| # | Primer name* | Application | Sequence |
|---|---|---|---|
| 27 | nAchR α9 siRNA2-F | shRNA | GATCCCCAAAGCAGCCAGGAACAAAGTTCAAGAGACTTTGTTCCTGGCTGCTTTTTTTA (SEQ ID NO: 13) |
| 28 | nAchR α9 siRNA2-R | shRNA | AGCTTAAAAAAAAGCAGCCAGGAACAAAGTCTCTTGAACTTTGTTCCTGGCTGCTTTGGG (SEQ ID NO: 14) |
| 29 | nAchR α5 siRNA1-F | shRNA | GATCCCCCCTGTATTGGGCTCTCATTTTCAAGAGAAATGAGAGCCCAATACAGGTTTTA (SEQ ID NO: 39) |
| 30 | nAchR α5 siRNA1-R | shRNA | AGCTTAAAAACCTGTATTGGGCTCTCATTTCTCTTGAAAATGAGAGCCCAATACAGGGGG (SEQ ID NO: 40) |
| 31 | nAchR α5 siRNA2-F | shRNA | GATCCCCCCGTCTTCGCTATCAACATTTCAAGAGAATGTTGATAGCGAAGACGGTTTTA (SEQ ID NO: 41) |
| 32 | nAchR α5 siRNA2-R | shRNA | AGCTTAAAAACCGTCTTCGCTATCAACATTCTCTTGAAATGTTGATAGCGAAGACGGGGG (SEQ ID NO: 42) |
| 33 | nAchR α9SC siRNA1-F | shRNA | GATCCCCGAGACGTGTTCGCTTTCTCTTCAAGAGAGAGAAAGCGAACACGTCTCTTTTA (SEQ ID NO: 43) |
| 34 | nAchR α9 SC siRNA1-R | shRNA | AGCTTAAAAAGAGACGTGTTCGCTTTCTCTCTTGAAGAGAAAGCGAACACGTCTCGGG (SEQ ID NO: 44) |
| 35 | nAchR α9 SC siRNA2-F | shRNA | GATCCCCGGGAACAAACAAGCACGAATTCAAGAGATTCGTGCTTGTTTGTTCCCTTTTA (SEQ ID NO: 45) |
| 36 | nAchR α9 SC siRNA2-R | shRNA | AGCTTAAAAAGGGAACAAACAAGCACGAATCTCTTGAATTCGTGCTTGTTTGTTCCCGGG (SEQ ID NO: 46) |
| 27 | nAchR α5 SC siRNA1-F | shRNA | GATCCCCTAGACGCGTTTTCTCTCGTTTCAAGAGAACGAGAGAAAACGCGTCTATTTTA (SEQ ID NO: 47) |
| 38 | nAchR α5 SC siRNA1-R | shRNA | AGCTTAAAAATAGACGCGTTTTCTCTCGTTCTCTTGAAACGAGAGAAAACGCGTCTAGGG (SEQ ID NO: 48) |
| 39 | nAchR α5 SC siRNA2-F | shRNA | GATCCCCATACACGTATGCCTCCTTCTTCAAGAGAGAAGGAGGCATACGTGTATTTTTA (SEQ ID NO: 49) |
| 40 | nAchR α5 SC siRNA2-R | shRNA | AGCTTAAAAAATACACGTATGCCTCCTTCTCTCTTGAAGAAGGAGGCATACGTGTATGGG (SEQ ID NO: 50) |
| 41 | Human nAchR α9-F | Real-time PCR | TACATCGCCAAGTGCCTC (SEQ ID NO: 51) |
| 42 | Human nAchR α9-R | Real-time PCR | TGTGACTAATCCGCTCTTGC (SEQ ID NO: 52) |
| 43 | Human GUS-F | Real-time PCR | AGTGTTCCCTGCTAGAATAGATG (SEQ ID NO: 53) |
| 44 | Human GUS-R | Real-time PCR | AAACAGCCCGTTTACTTGAG (SEQ ID NO: 54) |
| 45 | nAchR α9 Tet-off-F | Cloning | GTTGAATTCTATGAACTGGTCCCATTCCTGC (SEQ ID NO: 55) |
| 46 | nAchR α9 Tet-off-R | Cloning | GCGTCTAGACTAATCCGCTCTTGCTATGAT (SEQ ID NO: 56) |

*F = Forward, R = reverse, RT-PCR = reverse transcription-polymerase chain reaction, shRNA = short hairpin RNA, siRNA = short interfering RNA, nAChR = nicotinic acetylcholine receptor, GUS = β-glucuronidase.

A LightCycler thermocycler (Roche Molecular Biochemicals, Mannheim, Germany) was used for the real-time quantitative PCR. The α9-nAChR mRNA fluorescence intensity was measured and normalized to β-glucuronidase (GUS) expression using the built-in software (Roche LightCycler Version 4).

RNA Interference

Both α5- and α9-nAChR expression were each ablated in MDA-MB-231 breast cancer cell with at least two independent siRNAs. Scrambled sequences of each siRNA were used as controls (see Table 1). After BLAST analysis to verify the absence of significant sequence homologies with other human genes, the selected sequences were inserted into BglII and HindIII-cut pSUPER vectors to generate the pSUPER-Si α5-nAChR, pSUPER-Si α9-nAChR, and pSUPER-scramble vectors. The identities of all constructs were confirmed by DNA sequence analysis. The transfection protocol has been described previously (John M, Geick A, Hadwiger P, et al. Curr Protoc Mol Biol 2003; Chapter 26:Unit 26 2). Briefly, $1.5 \times 10^5$ cells were washed twice with phosphate-buffered saline and mixed with 0.5 μg of plasmid. One pulse was applied for a duration of 20 milliseconds under a fixed voltage of 1.2 kV on a pipette-type microporator MP-100 (Digital Bio, Seoul, Korea).

Generation of Stable nAChR-siRNA Expressing Cell Lines

At least three clones of the MDA-MB-231 cell lines were generated that stably expressed siRNAs to α5-nAChR or α9-nAChR or scrambled control siRNA. All experiments were performed using multiple subclones of each cell line, with reproducible results. The pSUPER-Si α5-nAChR, pSUPER-Si α9-nAChR, and pSUPER-scramble vectors were transfected, and stable integrants were selected 72 hours later with G418 (4 mg/mL). After 30 days in selective medium, two G418-resistant clones, referred to as Si α5-nAChR (Si α5) and Si α9-nAChR (Si α9), were isolated; these clones demonstrated greater than 80% reduction in mRNA and protein levels when compared with the control clones (scramble control, Sc).

In Vivo Treatment of Mice with α9-nAChR siRNA-Expressing Breast Cancer Cell Xenografts MDA-MB-231 cell lines with stable integration of pSUPER-Si α9 or pSUPER-Si α9 scramble sequences were established by G418 selection. The cells ($5 \times 10^6$) were implanted subcutaneously into each 6-week-old NOD.CB17-PRKDC(SCID)/J(NOD-SCID) mice (n=5) (purchased from National Science Council Animal Center, Taipei). After tumor transplantation, nicotine (10 mg/mL) was administered via the drinking water for 6 weeks until the mice were killed by anesthesia with ether. During the experiment, tumor size was measured using calipers and tumor volume was estimated by the formula: tumor volume $(mm^3) = \frac{1}{2} \times L \times W^2$, where L is the length and W is the width of the tumor (Lee W S, Chen R J, Wang Y J, et al. *Int J Cancer* 2003; 106(1):125-37). At the end of experiment, subcutaneous tumor masses were dissected from the mice and weighed. All mouse protocols were performed according to protocol approved by the Association for Assessment and Accreditation of Laboratory Animal Care (AALAC).

Generation of Nicotine- and NNK-Transformed MCF-10A Cells

MCF-10A cells were treated with a low dose of nicotine (10 μM) and NNK (1 μM) to mimic long-term exposure of cells to these carcinogens (Mei J, Hu H, McEntee M, et al. *Breast Cancer Res Treat* 2003; 79(1):95-105; Narayan S, Jaiswal A S, Kang D, et al. *Oncogene* 2004; 23(35):5880-9). Cells were subcultured every 4 days, and cells were treated with nicotine and NNK for 48 hours after every passage. After 2 months, the nicotine- and NNK-transformed cells (MCF-10A-Nic and MCF-10A-NNK) were transfected with adenoviruses carrying conditionally regulated (Tet-off) α9-nAChR transgenes.

Construction of α9-nAChR Adenovirus Tet-Off Expression Vectors

A PCR fragment encompassing the coding region of the α9-nAChR gene was generated using a forward primer, 5'-GTTGAATTCATGAACTGGTCCCATTCC TGC-3' (SEQ ID NO: 57), adapted with an EcoRI site and a reverse primer, 5'-GATGGATCCCTAATCCGCTCT TGCTATGAT-3' (SEQ ID NO: 58) that contained a BamHI site (see Table 1). After digestion with EcoRI and BamHI, the fragment was ligated into the pTRE-Shuttle vector. The integrity of the constructed vector was verified by restriction digestion and DNA sequence analysis. The Tet-responsive expression cassette was excised from the recombinant pTRE-Shuttle plasmids using the I-CeuI and I-SceI endonucleases and ligated into the predigested Adeno-X viral DNA. Recombinant Adeno-X viral DNA was propagated in *E. coli*, linearized by digestion with PacI, and transfected into low-passage HEK 293 cells. HEK 293 cells were infected with the recombinant virus and the growth medium was collected when 80 percent of the cells had detached from the culture plate to produce high-titer adenovirus stocks.

Generation of Adeno-X Tet-Off α9-nAChR-Overexpressing Cells

The nicotine- and NNK-transformed (MCF-10A-Nic and MCF-10A-NNK) cells were plated in 60-mm dishes at a density of $10^6$ cells per dish. Two days later, the cells were co-infected with the Tet-responsive recombinant virus and the tetracycline-controlled transactivator virus (BD Adeno-X Tet-off system, Clontech, Palo Alto, Calif.) at a multiplicity of infection of approximately five plaque forming units of each virus strain per cell. After incubation for 12 hours at 37° C. in a $CO_2$ incubator, the virus-containing medium was removed and fresh growth medium containing 10% serum was added in both the presence and absence of 1 μg/mL of the tetracycline analog doxycycline (DOX) (DOX+ or DOX−). This resulted in the establishment of MCF-10A-Nic (DOX) and MCF-10A-NNK (DOX) cells in which α9-nAChR gene expression was induced by removal of DOX.

Isolation of Transformed Adeno-X Tet-Off α9-nAChR Overexpressing Cells

The transformed MCF-10A-Nic (DOX) and MCF-10A-NNK (DOX) cells were plated onto soft agar (see below). After 21 days, colonies were isolated from soft agar and incubated with 0.5% trypsin for 10 minutes as in previous studies (Mei J, Hu H, McEntee M, et al. *Breast Cancer Res Treat* 2003; 79(1):95-105; Narayan S, Jaiswal A S, Kang D, et al. *Oncogene* 2004; 23(35):5880-9). Cells were dispersed in complete MCF-10A culture medium, maintained at 37° C., and cultured as cell lines.

Soft Agar Growth Assay

Anchorage-independent growth of α9-nAChR overexpressing (MCF-10A-Nic (DOX) and MCF-10A-NNK (DOX)) and siRNA-expressing MDA MB-231 Si α5, Si α9, and Sc cells were examined in soft agar assays. The base layer consisted of 0.9% low-melting point SeaPlaque agarose (Sigma, St. Louis, Mo.) in complete MCF-10A culture medium. Soft agar was composed of 0.4% SeaPlaque agarose in complete DMEM and F12 culture medium was mixed with $1 \times 10^4$ cells and plated on top of the base layer in 60-mm-diameter culture dishes. Cells were treated with NNK (1 μM) or nicotine (10 μM) prior to plating in soft agar. Soft agar cultures were maintained at 37° C. for an additional 21 days and observed for the appearance of colonies with a Leica DMI 4000B Microscope Imaging System (Leica Microsystems, Wetzlar, Germany). The assay was repeated four times with duplicate samples.

Nicotine- and NNK-Transformed MCF-10A Cells and Mice with α9-nAChR-Overexpressing, Nicotine-Transformed Xenografts BALB/c-nu/nu mice (female, 4 weeks old, n=5 per group) purchased from National Science Council Animal Center, Taipei, were injected subcutaneously with MCF-10A-Nic (DOX) and vector control ($5 \times 10^6$) cells. After transplantation, mice bearing tumors were treated with DOX (0.5 mg/mL) via drinking water for 14 days. After that, all mice bearing tumors (200 $mm^3$) were divided into either α9-nAChR mRNA expressing (DOX−) or non-induced (DOX+) groups, the latter of which could express the α9-nAChR mRNA at basal level. The mice were simultaneously treated with or without nicotine (10 mg/mL) in their drinking water for an additional 6 weeks. The xenografts were weighed and either snap-frozen in dry ice and stored at −80° C. for RNA and protein analysis or formalin-fixed and paraffin-embedded for immunohistochemical observation.

Protein Extraction, Western Blotting, and Antibodies

For determination of α9-nAChR protein expression, the Si α5, Si α9, Sc and MCF-10A-Nic (DOX+/−) cells were washed once with ice-cold phosphate-buffered saline and lysed on ice in cell lysis buffer (50 mM Tris-HCl, pH 8.0, 120 mM $NaCl_2$, 0.5% Nonidet P-40, 100 mM sodium fluoride, and 200 μM sodium orthovanadate) containing protease inhibitors, as previously described (Ho Y S, Chen C H, Wang Y J, et al. *Toxicol Appl Pharmacol* 2005; 205(2):133-48). Xenograft tumor tissues were thawed in 750 μL of lysis buffer containing protease inhibitors to examine protein expression. The samples were homogenized three times at seating 3 (18,000 rpm) on ice using a PRO 200 homogenizer (PRO Scientific Inc., Monroe, Conn.). Protein (50 μg) from each sample was resolved by 12% sodium dodecyl sulfate-polyacrylamide gel electrophoresis, transferred to a nitrocellulose membrane, and analyzed by western blotting. Mouse monoclonal anti-glyceraldehyde 3-phosphate dehydrogenase (GAPDH) antibody and rabbit polyclonal anti-α9-nAChR antibody were purchased from Abcam Inc (Cambridge, Mass.). Alkaline phosphatase-coupled anti-mouse and anti-rabbit IgG secondary antibodies were purchased from Santa Cruz Biotechnology (Santa Cruz, Calif.). The anti-GAPDH and anti-α9-nAChR primary antibodies were incubated at 1:2,000 and 1:8000 dilution, respectively, for 2 hours, and the secondary antibodies were incubated at 1:4,000 dilution for 1 hour. The assay was repeated twice with duplicate samples.

[$^3$H]-Nicotine Equilibrium Binding

L-(−)-[N-methyl-$^3$H]-nicotine (71-75 Ci/mmol) was purchased from Dupont/NEN Research Products (Boston, Mass.), and free base nicotine (99% pure) was purchased from the Eastman Kodak Co. (Rochester, N.Y.). To study the uptake of [$^3$H]-nicotine in MDA-MB-231 cell monolayers ($2 \times 10^6$ cells per well), cells were rinsed three times with a buffer containing 140 mM NaCl, 5.4 mM KCl, 1.8 mM $CaCl_2$, 0.8 mM $MgSO_4$, 5 mM glucose, and 25 mM Hepes (pH 7.4). Saturation binding studies were conducted for 2 hours at 37° C. in six-well plates, and used at least eight different concentrations of [$^3$H]-nicotine ranging from 1 to 15 nM. Time-dependent association kinetic studies in MDA-MB-231, Si α9, Sc cells were conducted using a single concentration of [$^3$H]-nicotine (7 nM) for treatments of 5, 10, 15, 30, 60 and 90 minutes. For determination of nonspecific binding, 10 μM unlabeled nicotine was pre-added to medium, after which cells were washed three times with ice-cold buffer and then exposed to [$^3$H]-nicotine. [$^3$H]-nicotine uptake was stopped by aspiration of the uptake medium and washing the wells three times with ice-cold buffer. The cells were lysed in 1 mL of 0.5% Triton X-100, and aliquots of the cell lysates were transferred to scintillation vials to determine the incorporated radioactivity by scintillation counting. The assay was repeated four times with duplicate samples.

Laser Capture Microdissection

Frozen sections from the breast tumor samples were prepared for laser capture microdissection experiments. In this study, tumor tissues diagnosed as different stages (stage 1-4, n=11) were collected. The sections stained with HistGene (Arcturus Engineering, Mountain View, Calif.) were subjected to laser capture microdissection by using a PixCell IIe system (Arcturus Engineering, Mountain View, Calif.) (Huang C, Yang L, Li Z, et al. *Cancer Genet Cytogenet* 2007; 175(1):19-25). The parameters used for laser capture microdissection included a laser diameter of 8 μm and laser power of 48-65 mW. For each specimen, 15,000 laser pulse discharges were used to capture ~10,000 morphologically normal epithelial cells or malignant carcinoma cells. Each population was visualized under a microscope to make sure that the captured cells were homogeneous. The caps with the captured cells were then fitted onto 0.5 mL Eppendorf tubes containing 42 μL of lysis buffer and RNA was isolated by following a standard protocol (PicoPure RNA Isolation Kit, Arcturus Bioscience, Mountain View, Calif.). The purified RNA was then measured by reverse transcription and real-time quantitative PCR analysis.

Immunohistochemistry and Confocal Microscopy

To investigate whether the α9-nAChR could be detected in human breast cancer cell lines, confocal microscopy assays were performed by seeding human breast cancer (MCF-7) cells onto poly-L-lysine-coated slides. The slides were incubated with FITC-labeled anti-α9-nAChR antibodies and rhodamine-labeled anti-caveolin-1 antibodies for 1 hour at room temperature, washed twice with phosphate-buffered saline, and incubated with secondary antibodies for an additional 30 minutes in a moist chamber at room temperature. The slides were then examined with a Leica TCS SP5 Confocal Spectral Microscope Imaging System (Leica Microsystems, Wetzlar, Germany).

The α9-nAChR protein localization in breast tumor tissues was further detected by immunohistochemistry. Paraffin-embedded breast tumor tissues that had been excised either from patients or from xenografted-tumors were cut into 8 μM slides. Sections were preincubated in 3% $H_2O_2$ and 0.3% Triton X-100 before microwaving for antigen retrieval. For α9-nAChR immunostaining, sections were microwaved in Tris buffer (pH 6) for 10 minutes. Following this step, sections were blocked in 5% horse serum (Chemicon, Temecula, Calif.) for 30 minutes and subsequently incubated with 1:400 diluted α9-nAChR antibody for 2 hours at room temperature. Following incubation with the primary antibodies, staining was developed according to the streptavidin-biotin-peroxidase method using a LSAB 2 kit purchased from DAKO (Carpinteria, Calif., USA). Briefly, sections were washed in phosphate-buffered saline, incubated with biotinylated anti-rabbit secondary antibody. They were then washed again in the same buffer and incubated in streptavidin-biotin-peroxidase complex. Staining was completed after incubation with substrate-chromogen solution. The length of incubation in solution with DAB was determined by low power microscopic inspection. Slides were then washed, dehydrated and coverslipped using DPX (Sigma-Aldrich, St. Louis, Mo.). Both adjacent sections and same slides were counterstained with hematoxylin for general histological orientation.

Statistical Methods

All data are expressed as means with 95% confidence intervals (CIs) of at least three determinations, unless stated otherwise. A paired t-test was used to compare α9-nAChR mRNA expression in paired normal vs tumor tissues from breast cancer patients. A Mann-Whitney test was used to evaluate the effects of α9-nAChR mRNA expression on cell lines and on growth of tumor xenografts with increased (Tet-off) or diminished (siRNA) α9-nAChR expression in mice. The fold ratios of α9-nAChR mRNA expression detected in tumor vs normal samples (from surgical or laser capture microscopy-dissected samples with different clinical staging criteria), were compared using the Scheffe test. Statistical differences in tumor cell proliferation, in vitro Tet-regulated α9-nAChR gene induction, [$^3$H]-nicotine receptor binding activity, and soft agar assays were analyzed by the Kruskal-Wallis (nonparametric) test, and each pairwise comparison was made with the Mann-Whitney test. All statistical comparisons were performed using SigmaPlot graphing software (San Jose, Calif.) and Statistical Package for the Social Sciences v.11.0.0 (SPSS, Chicago, Ill.). All statistical tests were two-sided. A P value of 0.05 or less was considered to indicate statistical significance.

Example 1 nAChR Expression in Human Breast Tumor Tissues and Breast Cell Lines

Expression of nAChR subunits in normal (nonmalignant) human breast cell lines (MCF-10A and HBL-100) and human breast cancer cell lines (MDA-MB-231, MDA-MB-453, AU-565, BT-483, and MCF-7) was characterized. To evaluate the expression of nAChR subunits among Taiwanese breast cancer patients, human breast tumors (n=50) and the surrounding normal tissues were dissected and subjected to RT-PCR separately. All breast cell lines were found to express similar (α5, α9, and α10) nAChR subunits (FIG. 1, A). The same three nAChR subunits (α5, α9, and α10) predominated in normal and malignant breast tissues (FIG. 1, B). We found increased α9-nAChR mRNA levels in nearly all tumor tissues compared with normal tissues (FIG. 1, G). By contrast, mRNA levels for the α5- and α10-nAChR subunits were not substantially different between tumor and normal paired samples.

Example 2

Role of α9-nAChR in Growth of Human Breast Cancer Cells

To explore the possibility that the α9-nAChR subunit might play a role in smoking-induced human breast tissue tumorigenesis, a stable MDA-MB-231 cell line in which the expression of α9-nAChR was reduced by RNA interference was established. An MDA-MB-231 cell line with reduced expression of the α5-nAChR subunit was also generated as a control (FIG. 1,C). A cell line in which expression of both the α5- and α9-nAChR subunits was silenced could not be established due to the essential role of these subunits in cell survival. Rates of cell proliferation in parental MDA-MB-231 cells (231) and in such cells stably transfected with scrambled vector (Sc) or α5-nAChR (Si α5) siRNAs were statistically significantly increased after treatment with 1 μM NNK or 10 μM nicotine (for Sc cells on day 11, mean $OD_{540\,nm}$ with DMSO=0.77, with nicotine=1.35 and with NNK=1.77; difference, nicotine vs control=0.58, 95% CI=0.48 to 0.68, P=0.009; difference, NNK vs control=1.00, 95% CI=0.9 to 1.1, P=0.009; for Si α5 cells on day 11, mean $OD_{540\,nm}$ with DMSO=0.77, with nicotine=1.35, and with NNK=1.78; difference, nicotine vs control=0.58, 95% CI=0.48 to 0.68, P=0.009; difference, NNK vs control=0.99, 95% CI=0.89 to 1.09, P=0.009) (FIG. 1,D). The rates of cell proliferation in Si α5 cells were statistically significant decreased after treatment with 10 μM nicotine, 1 μM NNK and vehicle control when compared to Sc cells (for DMSO treatment on day 11, mean $OD_{540\,nm}$ of Sc cells=0.77 and Si α9 cells=0.63; difference=1.34, 95% CI=0.027 to 0.241, P=0.009; for nicotine treatment on day 11, mean $OD_{540\,nm}$ of Sc cells=1.35 and Si 9 cells=0.63; difference=0.72, 95% CI=0.65 to 0.79, P=0.009; for NNK treatment on day 11, mean $OD_{540\,nm}$ of Sc cells=1.77 and Si α9 cells=0.62; difference=1.15, 95% CI=1.11 to 1.19, P=0.009).

The membrane-associated α9-nAChR protein was detected in human MCF-7 breast cancer cells by immunofluorescence staining followed by confocal microscopy (FIG. 1, E, arrowhead). These results suggest that breast cancer cell proliferation induced by tobacco-specific carcinogenic components (such as NNK or nicotine) could be mediated through the endogenous α9-nAChR receptor. To test this hypothesis, MDA-MB-231 cells were treated with [$^3$H]-nicotine to determine its ligand-receptor binding activity. The results demonstrated that the dissociation constant ($K_d$) of [$^3$H]-nicotine binding is 3 nM (FIG. 1,F, left panel) and that its maximum binding activity is attained at 60 minutes in MDA-MB-231 cells (FIG. 1, F, right panel). The mean [$^3$H]-nicotine binding activity was statistically significantly inhibited in (Si α9) MDA-MB-231 cells that had been transfected with α9-nAChR siRNA compared with parental cells or with MDA-MB231 cells that had been transfected with scrambled (Sc) control siRNA ([$^3$H]-nicotine bound by Si α9 cells=201.7 DPM, by parental cells=489.7 DPM, by Sc cells=450.6 DPM, difference, Si α9 vs parental=288 DPM, 95% CI=275 to 301 DPM, P=0.009; difference, Si α9 vs Sc=248.3 DPM, 95% CI=231 to 265.6 DPM, P=0.009).

Example 3

Expression of α9-nAChR mRNA in Human Breast Tumor Tissues

Figure 2:
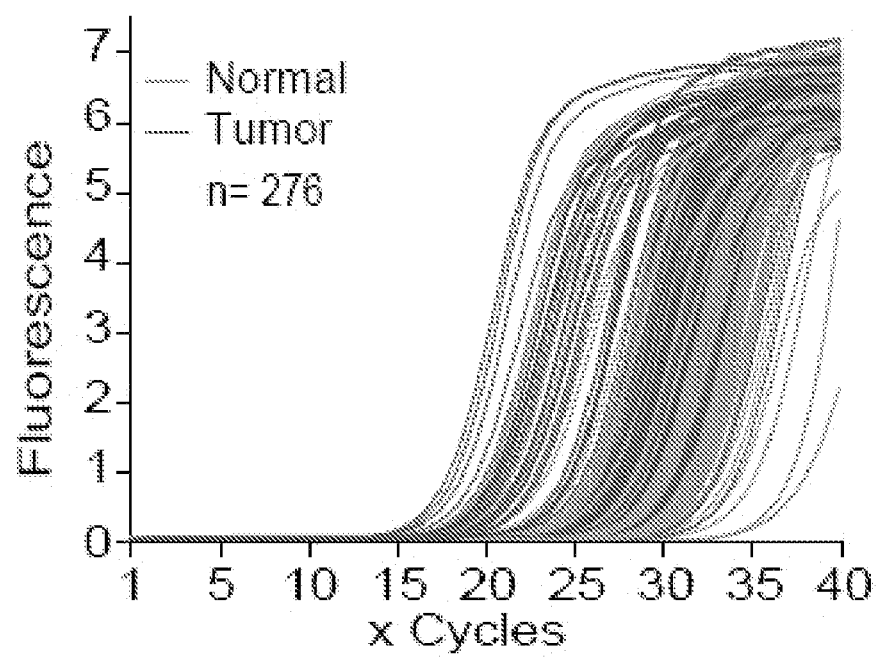
FIG. 2 shows α9-nicotinic acetylcholine receptor (α9-nAChR) expression levels in normal and malignant human breast tissues. A) The α9-nAChR mRNA expression profiles of paired human breast tumor (red lines) and normal (green lines) tissues (n=276) were detected by real-time polymerase chain reaction (PCR). B) α9-nAChR mRNA expression levels in 186 patient samples in which expression was higher in tumor than normal (T>N) vs 90 samples in which expression was higher in normal than tumor tissue (N>T). Copy numbers (×10$^5$ per μg mRNA) were calculated from mean real-time PCR data; error bars indicate the 95% confidence intervals. Normal vs tumor tissue in group 1 (T>N), P=0.002; normal vs tumor tissue in group 2 (N>T), P=0.16. Data were analyzed with paired t-test; P-values presented are two-sided. C) Paired tumor and normal tissue samples categorized according to the kind and degree of α9-nAChR mRNA expression differences. The levels of α9-nAChR mRNA calculated in FIG. 2, B were subdivided into four groups depending on the extent of the difference in expression between tumor and normal tissue (<2, 2-5, 5-10, and >10-fold). The percentage of occurrences and the total number of tumor-normal pairs are presented for each category. D) Relative expression of α9-nAChR mRNA in tumor and normal tissue pairs grouped according to clinical breast cancer stage. The tumor-normal tissue pairs for which relative levels of α9-nAChR mRNA were established in FIG. 2, B were divided into five subgroups according to clinical staging criteria as recommended by the American Journal of Critical Care (AJCC). Data shown are the mean of the fold ratios of expression in paired tumor and normal tissues. Error bars indicate 95% confidence intervals. The numbers of paired samples at each stage are indicated above the bars. Data were analyzed with an overall nonparametric test (Kruskal Wallis test), and multiple comparisons were assessed by Mann-Whitney test. The comparison was carried out as follows: stage 0 vs stage 1, P=0.66; stage 0 vs stage 2, P=0.047; stage 0 vs stage 3, P<0.001; stage 0 vs stage 4, P<0.001. All P-values are two-sided. D1) Fold differences in α9-nAChR mRNA expression levels in laser-capture microdissected tumor vs normal paired samples as detected by real-time-polymerase chain reaction. Data represent the mean fold ratios from laser capture microdissection-dissected samples with different clinical staging criteria from stage 1-4; error bars indicate 95% confidence intervals. Comparisons were performed for stage 1 vs stage 2 (P<0.001) and stage 1 vs stage 3 (P<0.001). Data were analyzed using an overall nonparametric test (Kruskal Wallis test), and multiple comparisons were made with the Scheffe test. All P-values are two-sided. D2) Analysis of α9-nicotinic acetylcholine receptor (α9-nAChR) expression in human breast carcinoma tissues. Immunolocalization of α9-nAChR protein in human ductal carcinoma in situ (DCIS) breast tumor tissues. The tumor tissues were cut into 8 μm serial sections, and then stained with antibodies specific to human α9-nAChR. N, normal; T, tumor; I.H.C., immunohistochemistry stain; H.E., hematoxylin and eosin stain. No statistically significant increase in α9-nAChR protein expression (brown-stain) was detected in early stage tumor tissues diagnosed as DCIS (FIG. 2, D2, red square frame, indicated by yellow arrows). As expected, normal tissues did not express substantial levels of α9-nAChR (FIG. 2, D2, green square frame, indicated by green arrows). Scale bar=200 μm. E) Immunolocalization of the α9-nAChR protein in human invasive ductal and lobular carcinoma breast tumor tissues. The tumor tissues were cut into 8 μm serial sections and stained with antibodies specific to human α9-nAChR. N, normal; T, tumor; I.H.C., immunohistochemistry stain; H.E., hematoxylin and eosin stain. The normal breast cells are indicated by green arrows in a green frame; whereas the malignant breast cells are indicated by yellow arrows in a red frame. Scale bar=200 μm.
Figure 2:
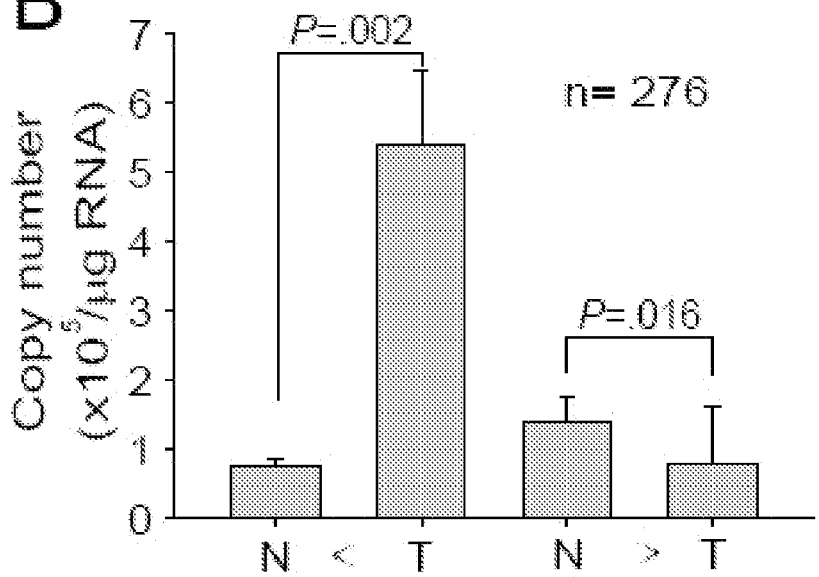
Figure 2:
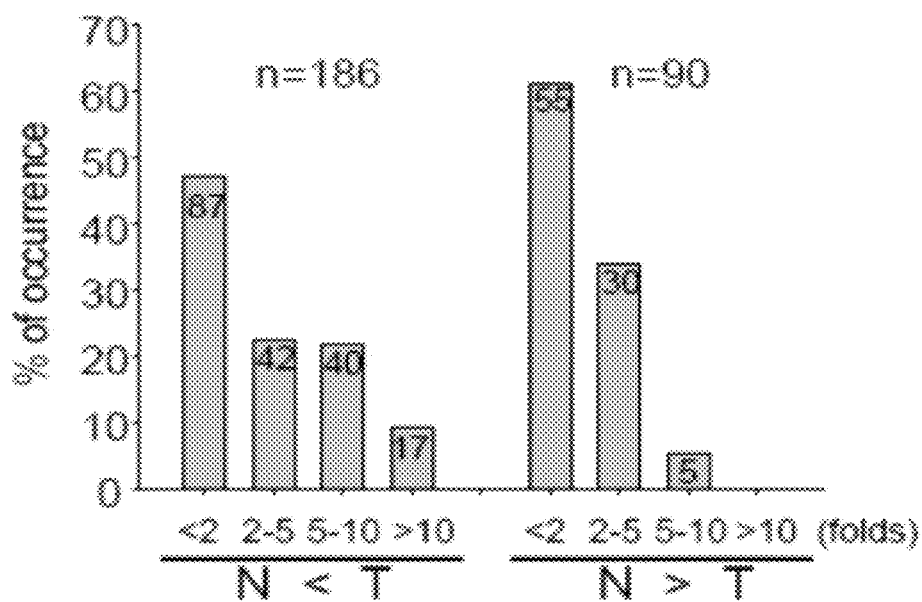
Figure 2:
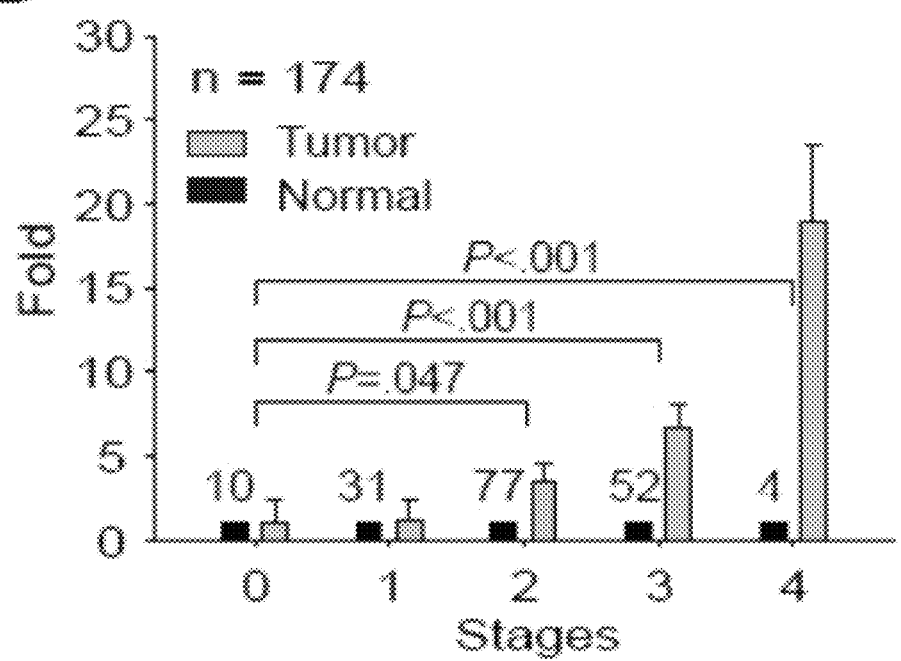
Figure 2:
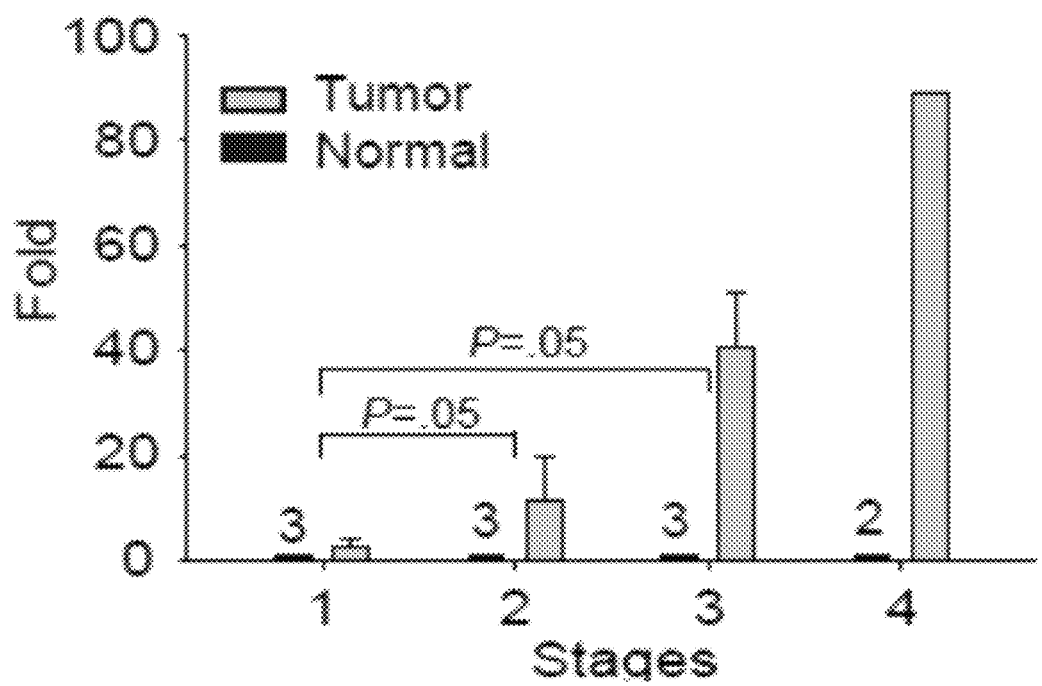
Figure 2:
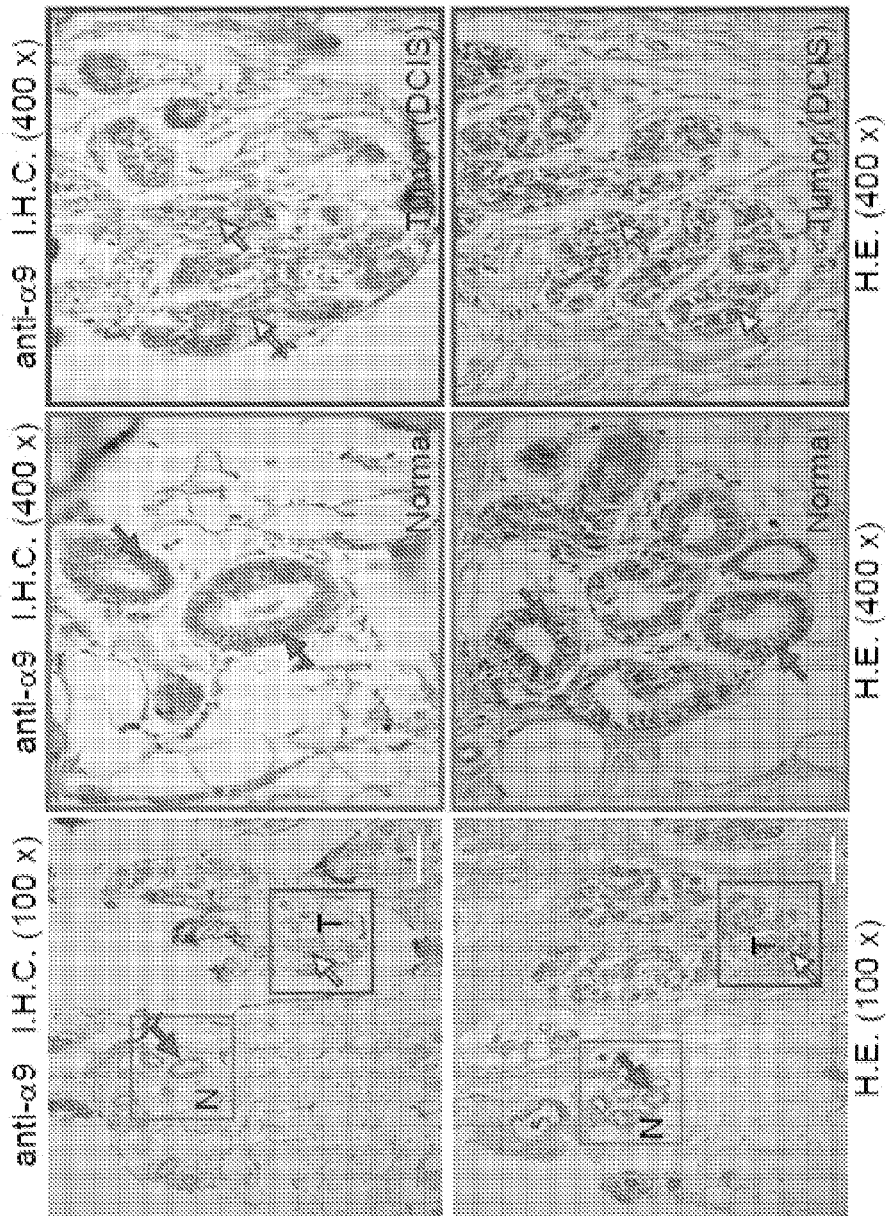
Figure 2:
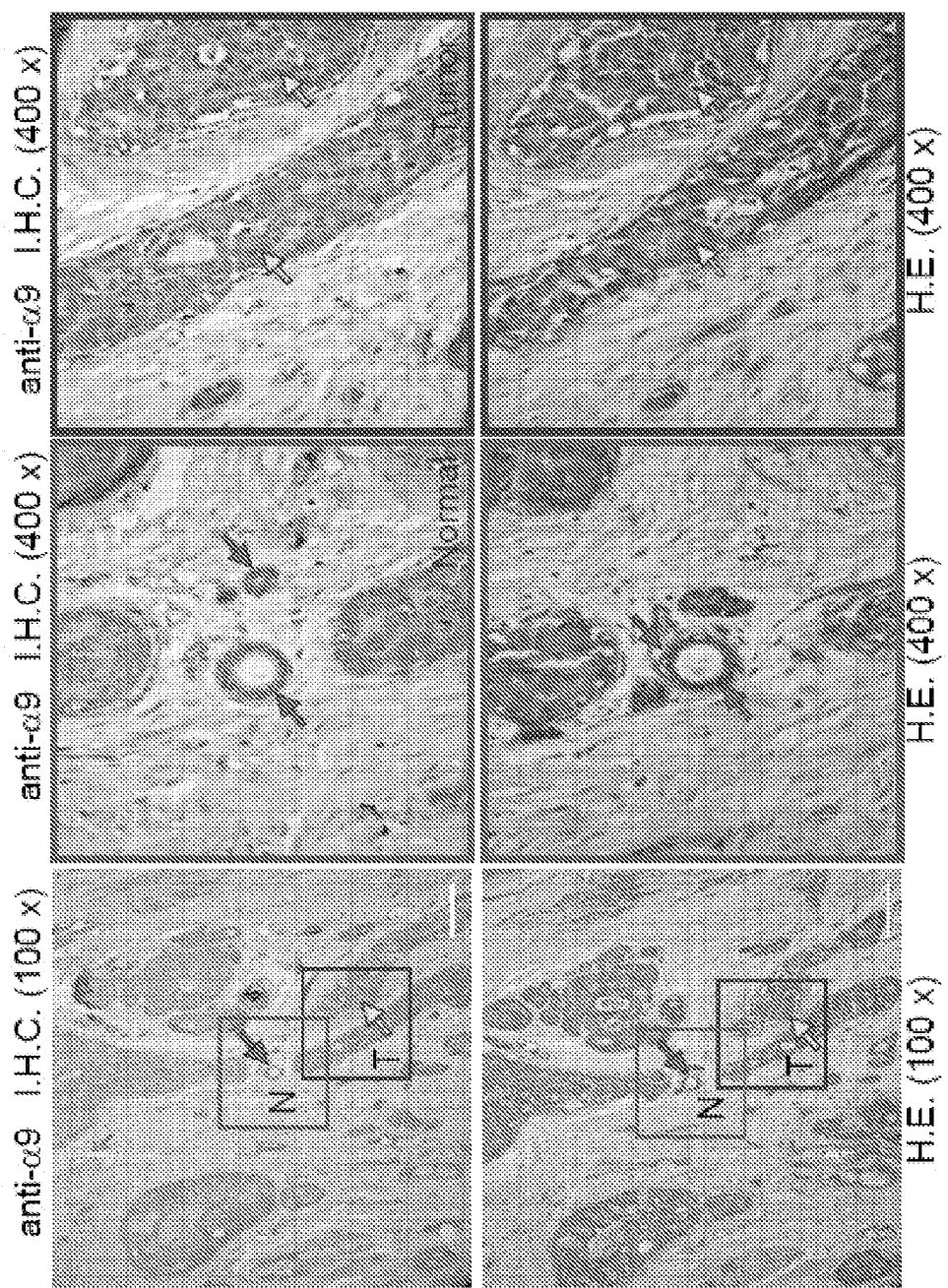

As described above, the α9-nAChR subunit is important for nicotine-induced breast cancer cell proliferation. The mRNA levels of the α9-nAChR subunit in 276 tumor vs normal paired tissue samples were examined by real-time PCR analysis (FIGS. 2, A and B). The PCR amplification curves were "left-shifted" in the tumor tissues (FIG. 2, A, red lines) relative to the profiles of normal tissues (green lines), indicating that the tumor samples overall contained greater quantities of α9-nAChR mRNA. The real-time PCR results were calculated and the tumors were divided into two groups according to their α9-nAChR mRNA expression patterns. Here, 186 of 276 (67.3%) normal vs tumor tissue pairs fell into the group in which expression of the α9-nAChR was higher in tumor than in normal tissue (T>N) and 90 (32.7%) paired samples had somewhat higher expression in normal than in tumor tissue (N>T) (FIG. 2, C). In the group with higher tumor than normal expression (T>N) overall, the α9-nAChR expression in tumor cells was 7.84-fold greater than that of normal cells (copy number for normal cells=73, 638 vs tumor cells=497,655, difference=424,017, 95% CI=285,647 to 709,664, P=0.002). Also, more than fivefold increased α9-nAChR mRNA expression was detected in 57 of 186 (30.6%) of the tumor tissues (FIG. 2, C, bars 3 and 4). However, in the group with higher normal than tumor expression (N>T), nearly all of the normal tissues had less than fivefold greater α9-nAChR expression than the paired tumor tissues (FIG. 2, C, bars 5 and 6).

Example 4

Expression of α9-nAChR in Advanced Stage Breast Tumor Tissues

Each tumor vs normal tissue pair was then categorized according to the clinical stage of the tumor (FIG. 2, D). Advanced-stage tumors were associated with substantially higher levels of α9-nAChR mRNA expression. Data are presented as comparisons of the means of the fold ratios between paired tumor vs normal tissues and compared at each stage with the fold change of α9-nAChR mRNA expression levels in stage 0 (ductal carcinoma in situ [DCIS]) tumor vs normal paired tissues, as follows: stage 0=1.0-fold, stage 1=1.14-fold, stage 2=3.51-fold, stage 3=6.66-fold, stage 4=18.88- fold; difference, stage 0 vs 1=0.14-fold, 95% CI=0.09 to 0.19-fold, P=0.66; difference, stage 0 vs 2=2.51-fold, 95% CI=1.39 to 3.63-fold, P=0.047; difference, stage 0 vs 3=5.66-fold, 95% CI=3.67 to 7.65-fold, P<0.001; difference, and stage 0 vs 4=17.88-fold, 95% CI=9.22 to 26.54-fold, P<0.001). To confirm these observations, laser capture-microdissected tumor and normal cells were harvested separately from 11 tumor samples. The α9-nAChR mRNA expression levels in the laser-capture microdissected cells were determined by real-time PCR analysis. The α9-nAChR mRNA expression level increased in a differentiation stage-dependent manner (stage 1=2.55-fold, stage 2=11.6-fold, stage 3=35.66-fold; difference, stage 1 vs 2=9.08-fold, 95% CI=1.85 to 16.3-fold, P=0.05; difference, stage 1 vs 3=33.1-fold, 95% CI=8.24 to 57.97-fold, P=0.05) (FIG. 2, D, and FIG. D1). Next, 9-nAChR protein localization was determined by immunohistochemical staining of frozen tumor sections, which revealed an increase in α9-nAChR protein expression in advanced-stage tumor tissues diagnosed as invasive ductal and lobular carcinomas (FIG. 2, E, brown stain in red square frame indicated by the yellow arrows). In contrast, normal tissues did not express substantial levels of α9-nAChR (FIG. 2, E, green square frame, indicated by the green arrows). In the present study, no substantial changes in α9-nAChR mRNA and protein expression levels were detected in premalignant ductal carcinoma in situ lesions (DCIS, diagnosed as stage 0) tumor vs normal paired samples (n=10) (FIG. 2, D, bars 1 and 2, and FIG. D2).

Example 5

Figure 3:
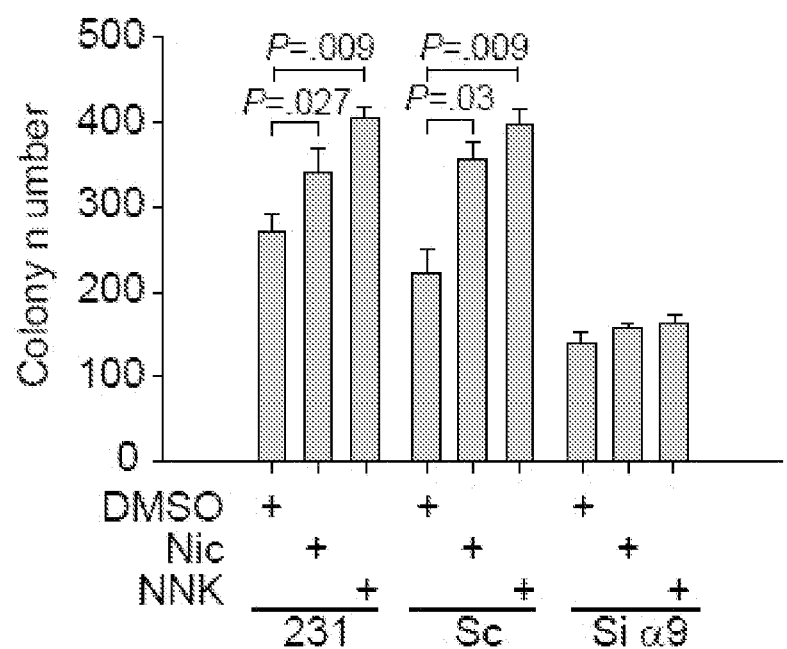
FIG. 3 shows tumorigenicity of MDA-MB-231 cells that express α9-nicotinic acetylcholine receptor short interfering RNAs (α9-nAChR siRNAs) as measured in soft agar assays and tumor growth in mice. A) Effect of α9-nAChR activation on anchorage-independent growth of MDA-MB-231 cells. Parental MDA-MB-231 cells (231) and cells that expressed α9-nAChR siRNA (Si α9) or a scrambled control siRNA (Sc) were treated with the nicotine metabolite, 4-(methylnitrosamino)-1-(3-pyridyl)-1-butanone (NNK; 1 μM) or nicotine (Nic; 10 μM) prior to plating in soft agar. The number of colonies in soft agar 21 days after plating 10,000 cells per 3 mm diameter dish was counted under the microscope after crystal violet staining. The experiment was repeated four times with duplicate samples. Data represent the means of nine samples in each group; error bars indicate the 95% confidence intervals. Statistically significant differences are shown for wild type MDA-MB-231 (231) cells exposed to dimethylsulfoxide (DMSO) vs nicotine (P=0.027) or DMSO vs NNK (P=0.009), and for scrambled vector control (Sc) cells exposed to DMSO vs nicotine (P=0.03) or DMSO vs NNK (P=0.009). Colony number was also statistically significantly higher for MDA-MB-231 (231) cells and scrambled vector control (Sc) cells compared with α9-nAChR siRNA-carrying cells (Si α9) whether treated with DMSO, nicotine, or NNK (P=0.009). Data were analyzed using nonparametric tests (Kruskal-Wallis and Mann-Whitney test); all P-values are two-sided. B) Effect of α9-nAChR activation on tumorigenesis by MDA-MB-231 cells in nude mice. Wild type 231 cells, Si α9 cells, or scrambled siRNA control cells (Sc) ($1\times10^7$) were injected subcutaneously into the back of each NOD.CB17-PRKDC (SCID)/J (NOD-SCID) mouse (n=5). After tumor transplantation, nicotine (10 mg/mL) was administered via drinking water for 6 weeks until the mice were killed. The gross appearance of the tumors was observed 6 weeks after drug treatment. C, D) Tumor volumes and weights in mice from (B). Tumor samples from each group were analyzed. Data represent the mean tumor volume (C) and tumor weight (D) for 10 mice per group. Error bars indicate the 95% confidence intervals. In (C), tumors from MDA-MB-231 cells with α9-nAChR siRNA (Si α9) were statistically significantly smaller than those from parental (231) or control (Sc) cells with or without nicotine treatment (P=0.009). In (D) tumors in nicotine-treated mice that were injected with MDA-MB-231 (231) cells (P=0.027) or scrambled vector control (Sc) cells (P=0.009) were heavier if the mice were fed nicotine. In comparison, tumors in mice that had been injected with MDA-MB-231 cells containing α9-nAChR siRNA (Si α9) were statistically significantly smaller than both of the other groups in the presence or absence of nicotine treatment (P=0.009). Data were analyzed by nonparametric tests (Kruskal Wallis and Mann-Whitney test); all P-values are two-sided. E) Expression of nAChR subunits in tumors with silencing RNAs. Tumors were dissected from mice at the end of the experiment. Total RNA and protein lysates were isolated from the tumor tissues, and α9- and α5-nAChR mRNA and protein expression were detected by reverse transcription-polymerase chain reaction (RT-PCR) and by western blotting (WB), respectively. β-glucuronidase (GUS) and glyceraldehyde 3-phosphate dehydrogenase (GAPDH) expression served as controls. The Si α9 group was statistically significantly different from both the Sc and 231 groups (P=0.009).
Figure 3:
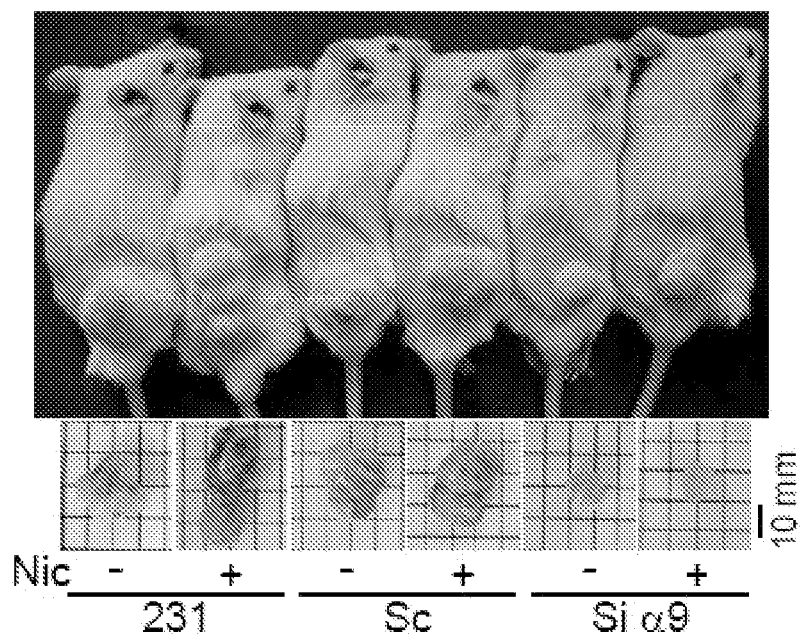
Figure 3:
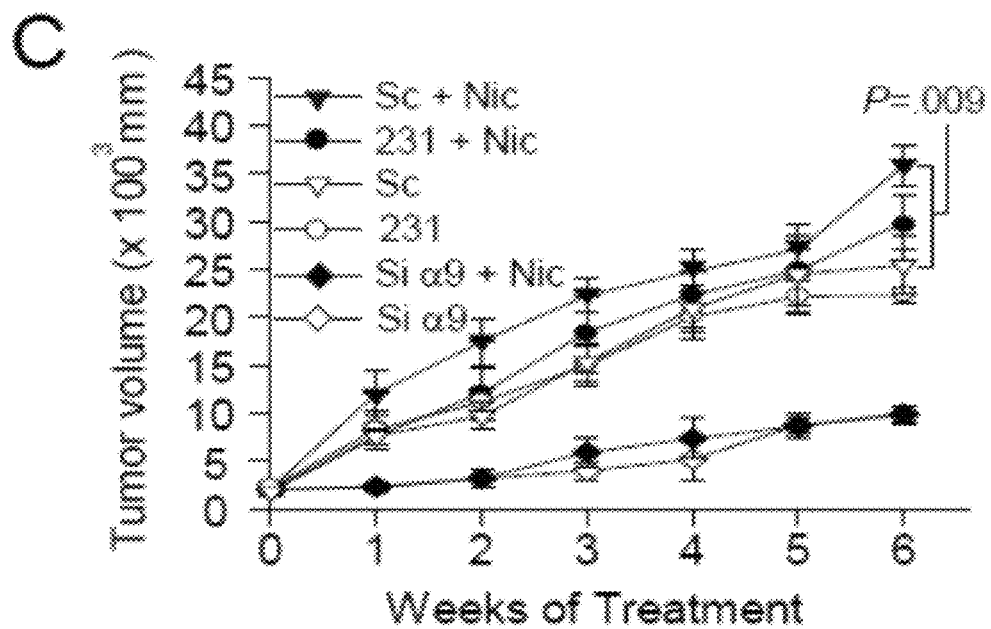
Figure 3:
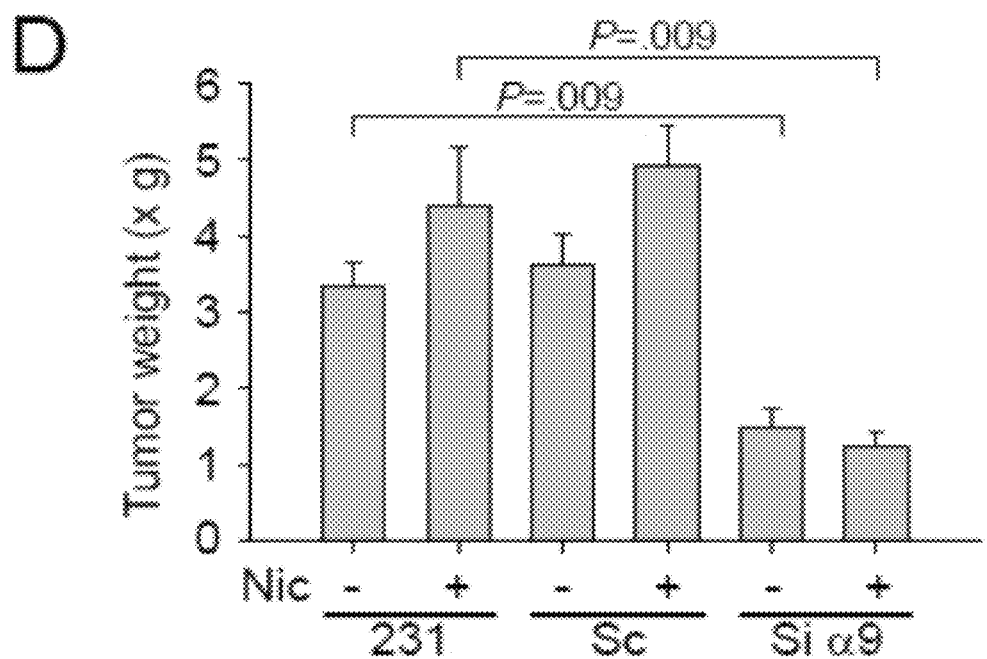
Figure 3:
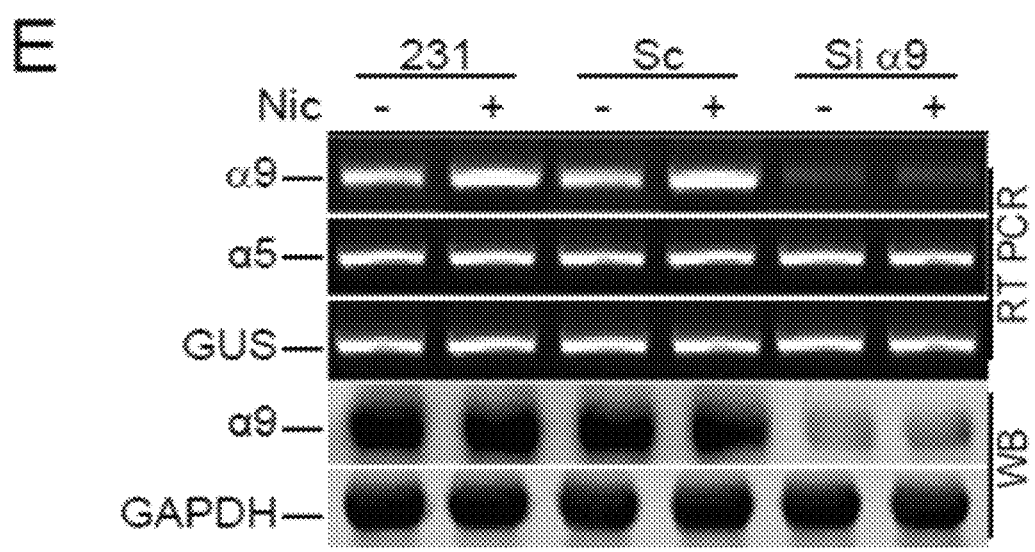

Influence of α9-nAChR Expression on Growth of MDA-MB-231 Cells in Transformation Assays In soft agar assays, the number of transformed colonies was statistically significantly reduced in MDA-MB-231 cells that carried α9-nAChR siRNA (Si α9) (FIG. 3, A, bars 1, 4 and 7; no. of colonies: Si α9 cells=140, Sc cells=222, parental MDA-MB-231 cells=272; Si vs parental=132 colonies, 95% CI=93 to 170 colonies, P=0.009); Si α9 vs Sc=82 colonies, 95% CI=33 to 130 colonies, P=0.009). After treatment with nicotine and NNK, a statistically significant increase in the number of transformed colonies arising from parental MDA-MB-231 cells and from those carrying the scrambled control siRNA (Sc) compared with those carrying α9-nAChR siRNA (Si α9) was observed (FIG. 3, A). After nicotine treatment, colony numbers increased particularly in α9-nAChR-expressing cells (bars 2, 5 and 8; no. of colonies: Si α9 cells=157, Sc cells=357, parental cells=341; Si α9 vs parental=184 colonies, 95% CI=137 to 230 colonies, P=0.009; Si α9 vs Sc=200 colonies, 95% CI=164 to 235 colonies, P=0.009). After NNK treatment, colony numbers increased most in α9-nAChR-expressing cells (bars 3, 6 and 9; no. of colonies: Si α9 cells=164, Sc cells=398, parental cells=406; Si α9 vs parental=242 colonies, 95% CI=218 to 266 colonies, P=0.009; Si α9 vs Sc=234 colonies, 95% CI=202 to 266 colonies, P=0.009). The effects of α9-nAChR siRNA on cell growth in vivo was examined by treating SCID mice bearing MDA-MB-231, Sc, or Si α9 tumor xenografts with nicotine (10 mg/mL) in their drinking water. After 6 weeks, the tumor volumes and tumor weights in nicotine-treated MDA-MB-231 Si α9-tumor bearing mice were statistically significantly smaller than those in the nicotine-treated parental MDA-MB-231-tumor bearing mice (n=5 mice per group; tumor volume at 6 weeks treatment, mice with Si α9 tumors vs mice with parental cell tumors, 995.6 mm$^3$, vs 2993.2 mm$^3$, difference=1997.6 mm$^3$, 95% CI=1705 to 2290.2 mm$^3$, P=0.009; tumor weight at 6 weeks, mice with Si α9 tumors vs mice with parental cell tumors, 1.23 g vs 4.38 g, difference=3.14 g, 95% CI=2.31 g to 3.97 g, P=0.009) (FIG. 3, C). The tumor tissues were dissected from mice 6 weeks after tumor cell transplantation, and RT-PCR and western blot analysis revealed substantial inhibition of α9-nAChR mRNA and protein levels in tumors with α9-nAChR siRNA (FIG. 3, E). The mRNA expression level of α5-nAChR was unaltered in the same tumors (FIG. 3, E).

Example 6

Figure 4:
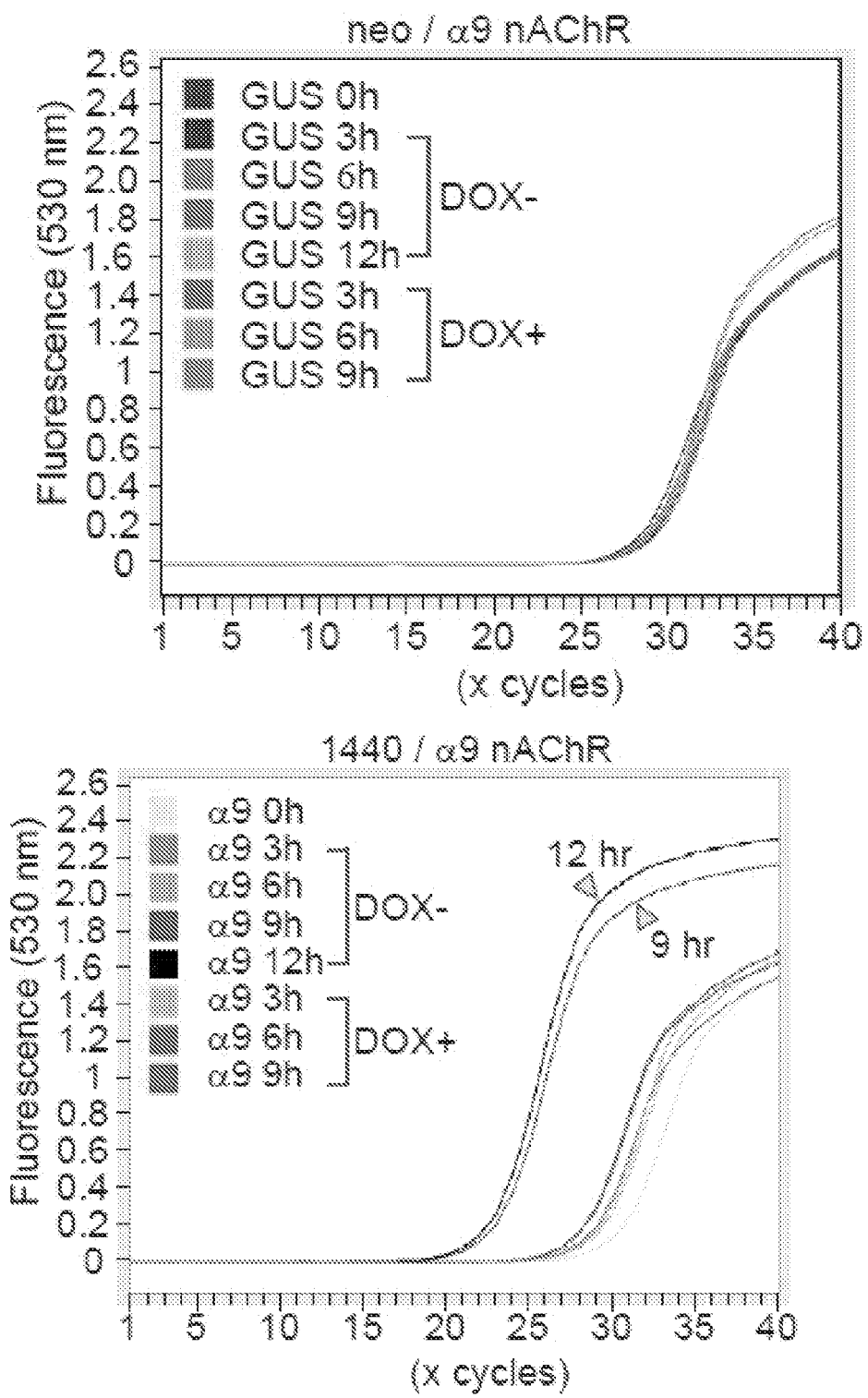
FIG. 4 shows establishment of transformed human breast epithelial MCF-10A (DOX) cells that overexpressed the α9-nicotinic acetylcholine receptor α9-nAChR) via a tetracycline-based (Tet-off)-regulatory system. A, B) Inducible α9-nAChR expression. Human MCF-10A (DOX) cells were cultured in fresh growth medium containing 10% serum and 1 μg/mL of the tetracycline analog, doxycycline (DOX+). α9-nAChR mRNA expression was induced in MCF-10A (DOX) cells (designated as 1440) in a time-dependent manner after removal of DOX. Cells infected with adenovirus vector alone (designated as neo) were used as a control. Data points represent the means; error bars indicate 95% confidence intervals. Inducible α9-nAChR expression was compared in MCF-10A (DOX–) cells at 0 vs 9 and 12 hours (P=0.009). β-glucuronidase (GUS) gene expression from each sample was analyzed for internal control. Data were analyzed using nonparametric tests (Kruskal Wallis and Mann-Whitney test); all P-values are two-sided. C) The level of α9-nAChR protein expression in MCF-10A (DOX–) cells increased substantially 24 hours after removal from DOX (lanes 1-4) in comparison to control MCF-10A (DOX+) cells (lanes 5-8).
Figure 4:
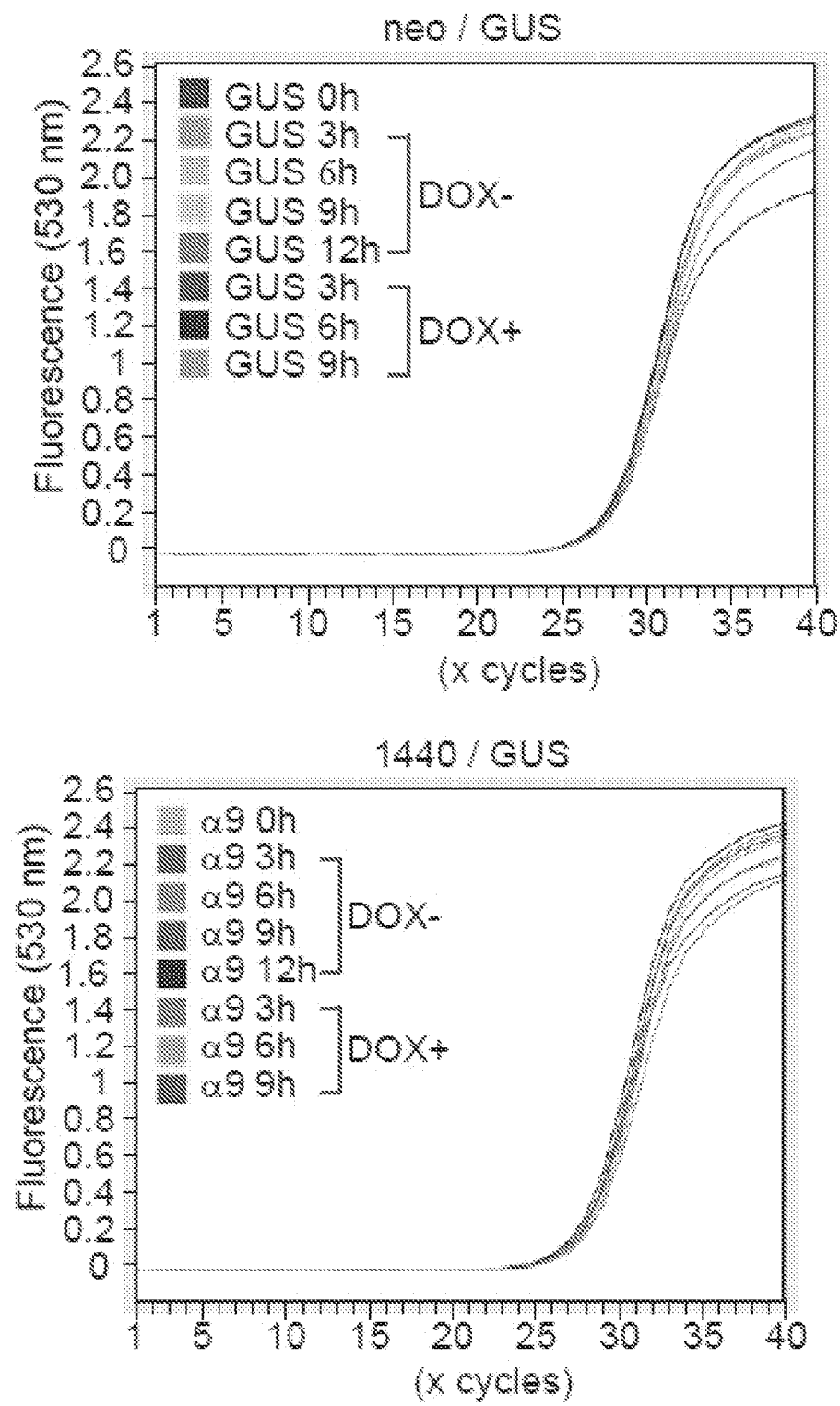
Figure 4:
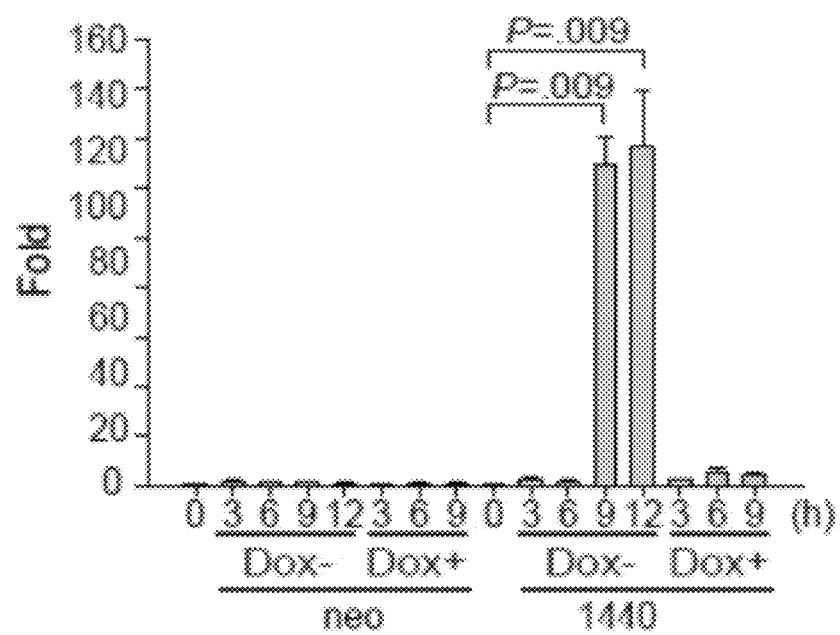
Figure 4:
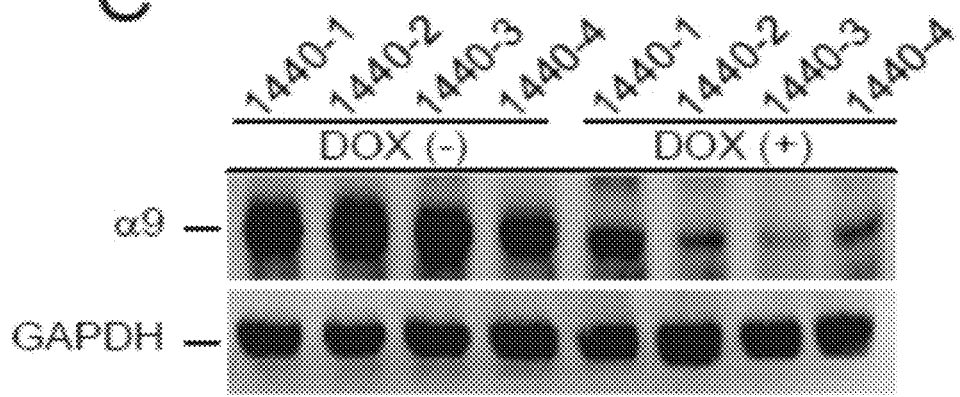

Effect of Overexpression of α9-nAChR on Transformation of Normal Human Breast Epithelial Cells and Tumor Growth in MCF-10A-Xenografted Mice To investigate whether α9-nAChR is involved in smoking-induced transformation in normal human breast epithelial (MCF-10A) cells, MCF-10A (DOX) cells in which α9-nAChR gene expression was induced by removal of DOX were established. Real-time PCR analysis revealed that α9-nAChR mRNA expression in MCF-10A (DOX-) cells was maximally (>200-fold) induced 9-12 hours after removal of DOX (FIG. 4, A, upper right panel, and FIG. 4, B, P=0.009). After 24 hours of removal of DOX, the levels of α9-nAChR protein were still substantially increased in MCF-10A (DOX-) cells compared with control MCF-10A (DOX+) cells (FIG. 4, C, lanes 1-4). The α9-nAChR-overexpressing MCF-10A (DOX-) cells exhibited increased cell proliferation compared with control MCF-10A (DOX+) cells (FIG. 5,A, empty vs solid triangle, day 7, mean OD$_{540}$ for DOX+ cells=1.53, for DOX- cells=2.65, difference=1.12, 95% CI=1.01 to 1.23, P=0.009). However, nicotine or NNK treatment induced cell proliferation was observed only in the MCF-10A (DOX+) cell line that expressed normal levels of the α9-nAChR.

Figure 5:
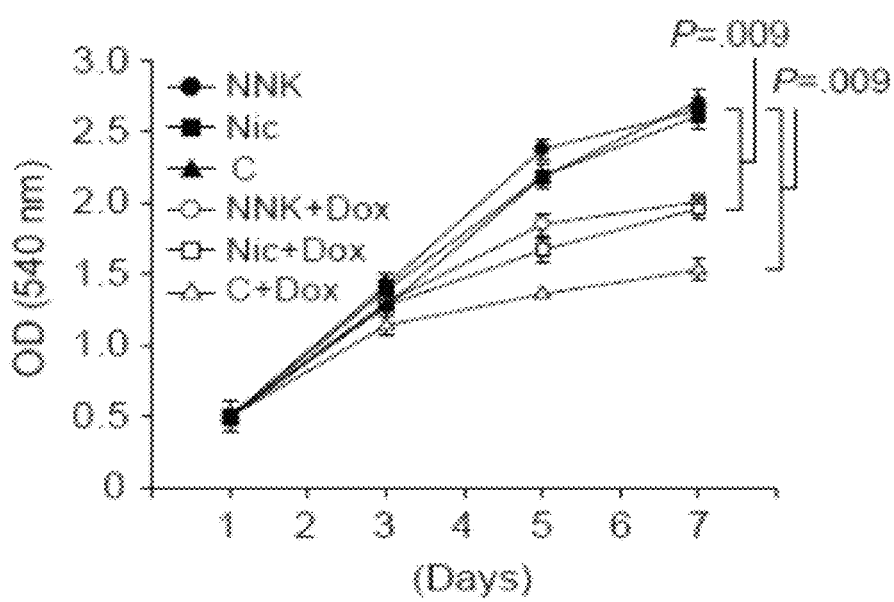
FIG. 5 shows effect of increased α9-nicotinic acetylcholine receptor (α9-nAChR) expression on tumorigenicity of MCF-10A cell xenografts in mice. A) Proliferation of MCF-10A human breast cancer cells on inducible expression of the α9-nAChR by removal of doxycycline (DOX). Cells were treated with nicotine (Nic; 10 μM) or the nicotine metabolite, 4-(methylnitrosamino)-1-(3-pyridyl)-1-butanone (NNK; 1 μM) in the presence or absence of DOX (1 μg/mL) for the indicated times, and then cell proliferation was detected with the 3-(4,5-dimethylthiazol-2-yl)-2,5-diphenyltetrazolium (MTT) assay. Cells treated with dimethylsulfoxide (DMSO) in the presence or absence of DOX were added as a control group. Data points represent the mean; error bars indicate 95% confidence intervals. Comparisons were performed for DMSO+DOX+ vs DMSO+DOX– (P=0.009), Nic+DOX+ vs Nic+DOX– (P=0.009), and NNK+DOX+ vs NNK+DOX– (P=0.009). The experiment was repeated four times with duplicate samples. Data were analyzed with nonparametric tests (Kruskal-Wallis and Mann-Whitney test); all P-values are two-sided. B) Transformation of human MCF-10A (DOX) cells by treatment with NNK (1 μM) or nicotine (10 μM) for 60 days. The NNK- and nicotine-transformed MCF-10A (DOX) cells were then cultured in soft agar in the presence or absence of DOX to evaluate anchorage-independent colony formation. C) In vivo tumorigenicity by MCF-10A (DOX) cells. BALB/c-nu/nu mice (female, 4 weeks old, n=20) were injected subcutaneously with $5\times10^6$ MCF-10A-Nic (DOX) cells per mouse. After transplantation, mice bearing tumors were treated with DOX (0.5 mg/mL) via drinking water for 14 days. After that, all mice bearing tumors (200 mm$^3$) were divided into either α9-nAChR mRNA expressing (DOX–) or non-expressing (DOX+) groups in the presence or absence of nicotine (10 mg/mL) in their drinking water (n=5, per group). The red arrow indicates withdrawal from DOX beginning at day 15. Data represent the mean tumor volume for 10 mice per group. Error bars represent 95% confidence intervals. Comparisons were performed for DOX+ Nic– vs DOX+ Nic+ (P=0.009) and DOX+ Nic+ vs DOX+ Nic+ (P=0.016). Data were analyzed by a nonparametric test (Kruskal Wallis and Mann-Whitney test); all P-values are two-sided. D) Expression of α9-nAChR subunits in MCF- 10A (DOX+ or −) tumors. At the end of the experiment in (C), the mice were killed and the tumors dissected to determine the levels of α9-nAChR mRNA and protein by using reverse transcription-polymerase chain reaction (RT-PCR) or western blotting (WB), respectively. Glyceraldehyde 3-phosphate dehydrogenase (GAPDH) expression served as a control. E) Immunolocalization of α9-nAChR protein in MCF-10A-Nic (DOX)-xenografted breast tumor tissues. Strong immunoreactivity for α9-nAChR was detected in the DOX− but not the DOX+ mouse tumor tissues (arrowhead). Scale bar=100 μm; C, vehicle control; Tet-off, removal of tetracycline (DOX).
Figure 5:
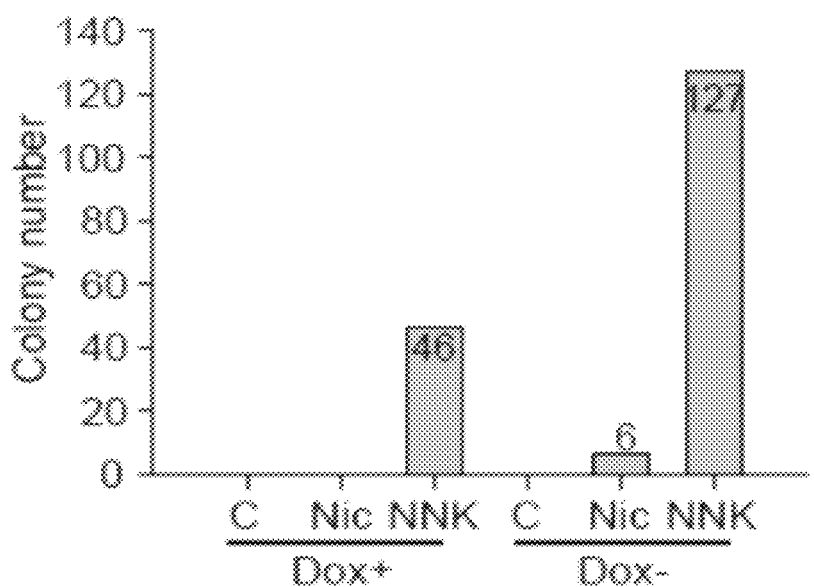
Figure 5:
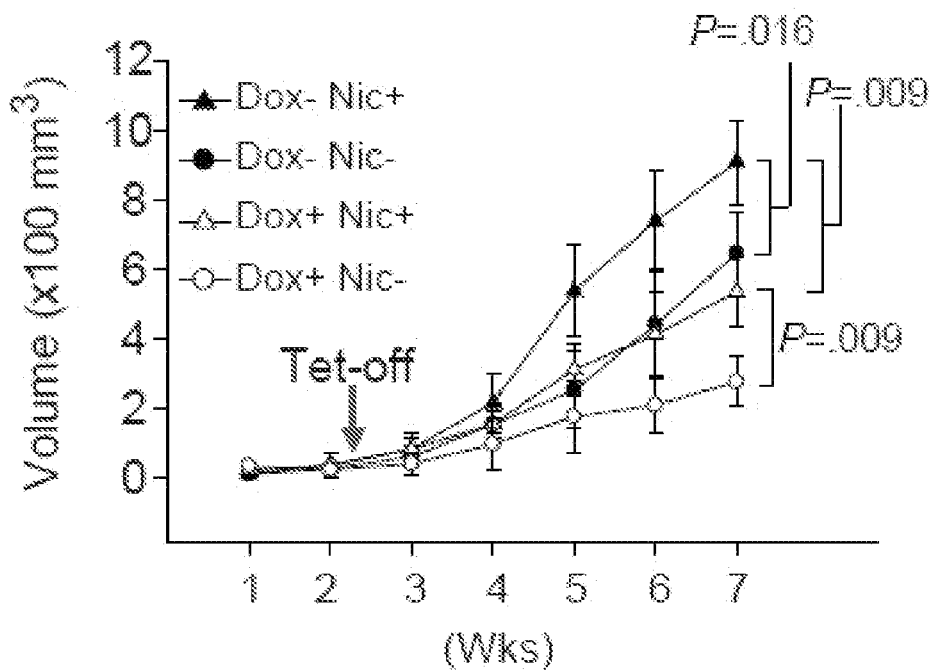
Figure 5:
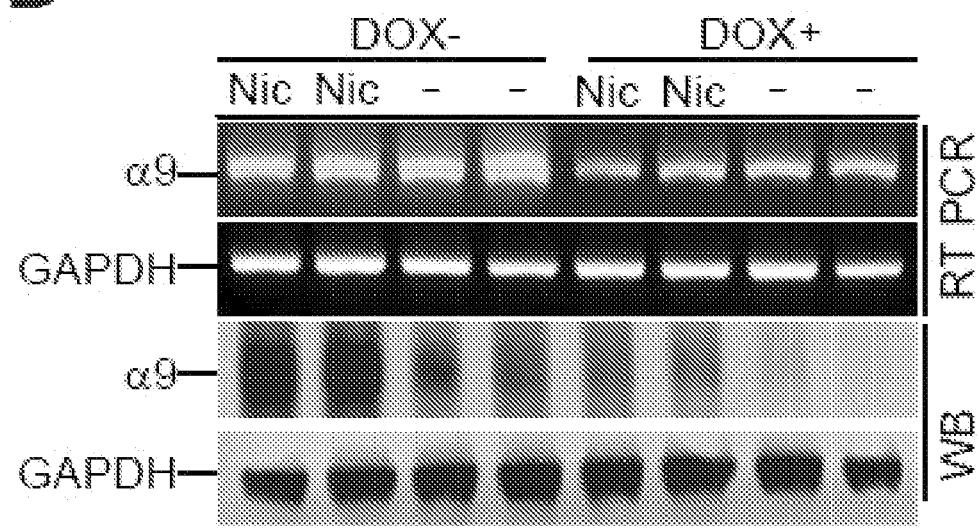
Figure 5:
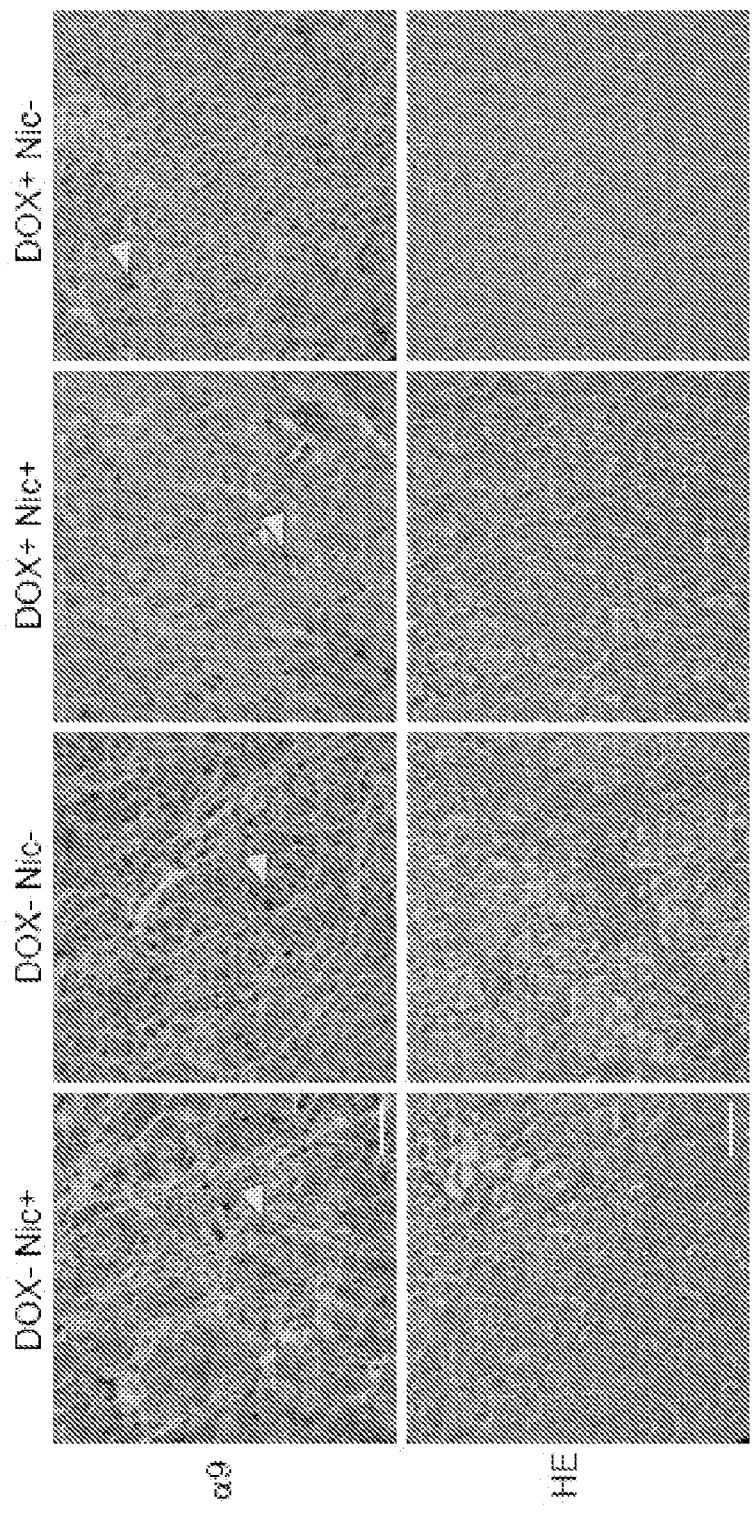

Previous studies in an animal model revealed that normal human breast epithelial (MCF-10A) cells can also be transformed by NNK in vivo (Mei J, Hu H, McEntee M, et al. *Breast Cancer Res Treat* 2003; 79(1):95-105). To mimic the long-term carcinogenic effects of nicotine to receptor binding on normal human breast epithelial cell transformation, MCF-10A (DOX+ or DOX-) cells were treated long-term (60 days) with NNK (1 µM) or with nicotine (10 µM) according to the methods described in Mei J, Hu H, McEntee M, et al. *Breast Cancer Res Treat* 2003; 79(1):95-105. The NNK- or nicotine-treated MCF-10A (DOX+ or DOX-) cells were then cultured in soft agar for an additional 21 days, and colony formation was evaluated microscopically (FIG. 5,B). More colonies were formed by NNK-treated MCF-10A (DOX-) cells compared with NNK-treated MCF-10A (DOX+) cells (FIG. 5, B, bars 6 vs 3). Interestingly, six colonies formed in the nicotine-treated MCF-10A (DOX-) cells (FIG. 5, B, bar 5), an observation that had never been reported previously (Mei J, Hu H, McEntee M, et al. *Breast Cancer Res Treat* 2003; 79(1):95-105). The results indicate that long-term exposure to lower concentrations of nicotine can induce transformation of normal breast epithelial cells and that α9-nAChR may play an important role in this process.

Figure 6:
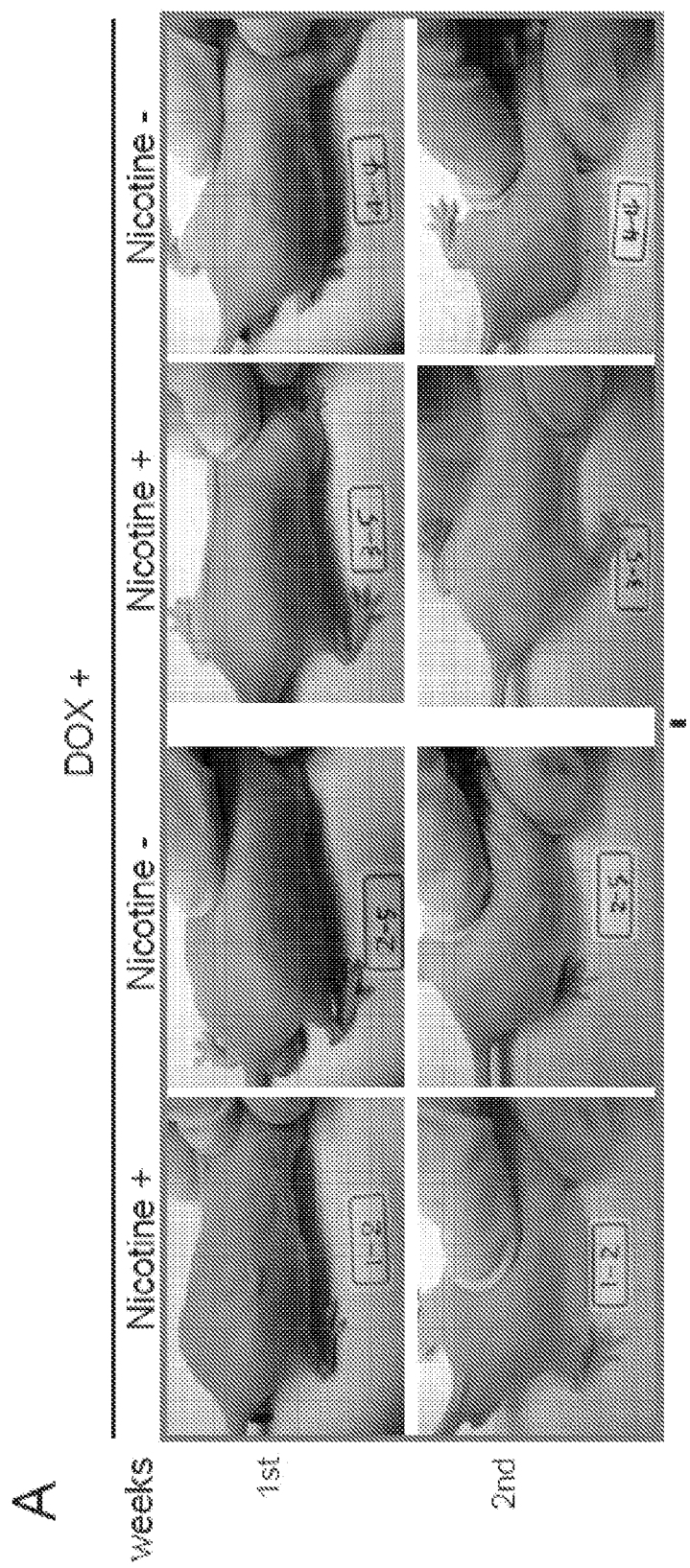
FIG. 6 shows in vivo treatment of mice bearing nicotine-transformed MCF-10A cell xenografts and overexpression of the α9-nicotinic acetylcholine receptor α9-nAChR) in response to doxycycline (DOX) removal. In the present study, the MCF-10A-Nic (DOX) transformed cell line was generated from soft agar colonies treated long-term with nicotine. The α9-nAChR gene expression was induced by removal of DOX (DOX−). A) Four representative female BALB/c-nu/nu mice (green square frame) from each group were injected subcutaneously with MCF-10A-Nic (DOX) ($5 \times 10^6$) cells. Adenovirus vector-transfected MCF-10A (neo) cells were also injected into mice as a negative control (data not shown). Mice with established tumors were treated with DOX (0.5 mg/mL) in the presence or absence of nicotine (10 mg/mL) in their drinking water until the tumors reached a mean size of 200 mm³. B) The mice described above were subdivided into two groups, designated DOX− and DOX+ (represented by the red and green square frames, respectively) according to the regulation of α9-nAChR mRNA expression. The mice were consecutively treated with or without nicotine in their drinking water (nicotine+, 10 mg/mL, vs nicotine−) for an additional 5 weeks.
Figure 6:
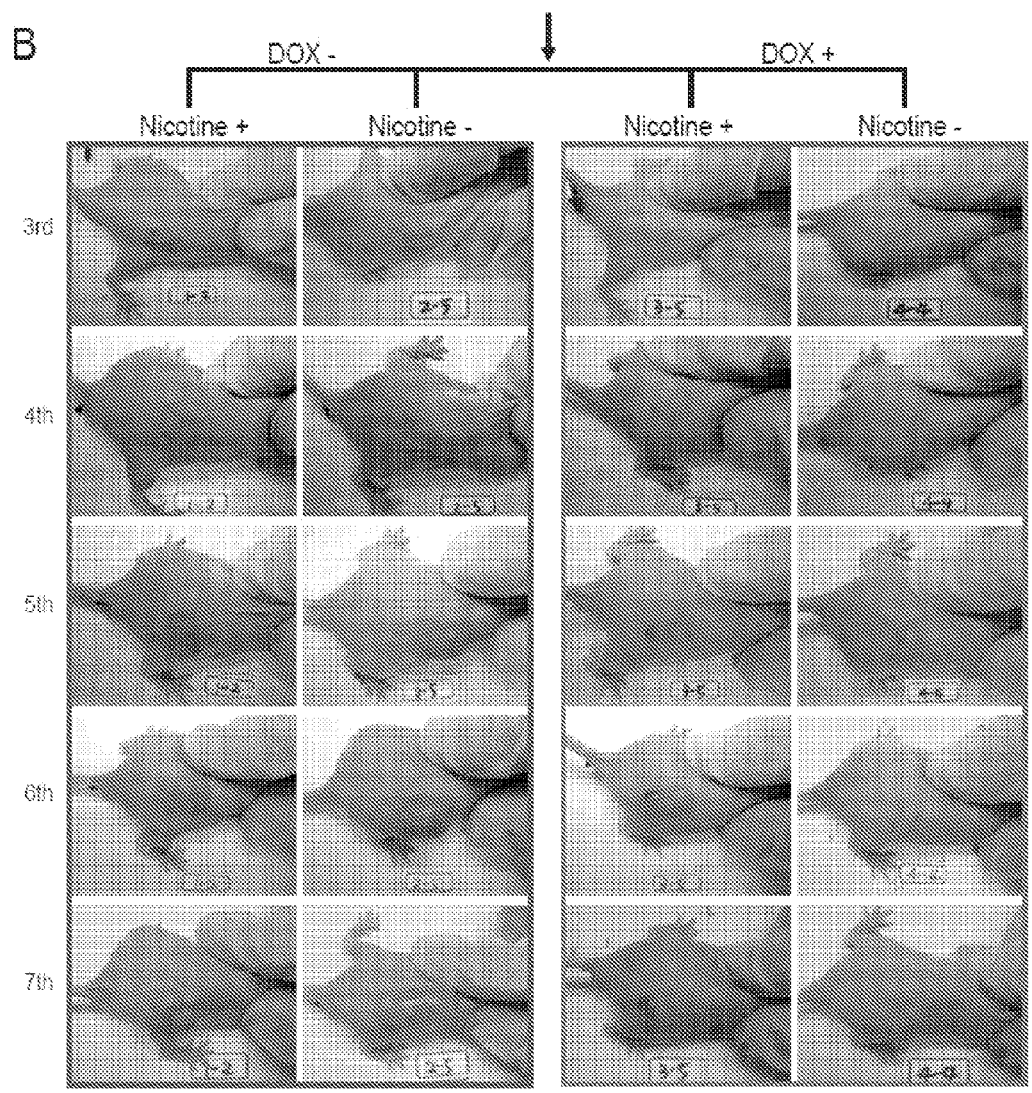

Two transformed cell lines were generated from soft agar colonies exposed to long-term treatment with nicotine or NNK: MCF-10A-Nic (DOX) and MCF-10A-NNK (DOX) (FIG. 5, B, bars 5 and 6). Examination was conducted as to whether induction of α9-nAChR in the presence or absence of nicotine stimulation in vivo would effectively promote tumor growth (FIG. 6). BALB/c-nu/nu mice (female, 4 weeks old) were injected subcutaneously with transformed MCF-10A-Nic (DOX) cells (5×10$^6$). After that, all mice bearing tumors (200 mm$^3$) were divided into either α9-nAChR mRNA expressing (DOX-) or non-expressing (DOX+) groups in the presence or absence of nicotine (10 mg/mL) in their drinking water (n=5, per group). A weekly measured tumor volume of MCF-10A-Nic (DOX)-xenografts in nude mice was statistically significantly increased after 7 weeks of nicotine treatment (+DOX, tumor volume without nicotine=266.2 mm³ vs with nicotine=501.6 mm³, difference=235.4 mm³, 95% CI=112.7 to 358 mm³, P=0.009) (FIG. 5, C, empty circle vs empty triangle symbol). Tumor growth induction in the nicotine-treated mice was potentiated by withdrawal of DOX (−DOX, tumor volume without nicotine=621.2 mm³ vs with nicotine=898.6 mm³, difference=277.4 mm³, 95% CI=98.1 to 456.7 mm³; P=0.016; with nicotine, DOX+ vs DOX−=501.6 mm³ vs 898.6 mm³, difference=397 mm³, 95% CI=241.3 to 552.6 mm³, P=0.009) (FIG. 5, C, empty triangle vs solid triangle symbol, and FIG. 6). No tumors were observed in the vector control mice in either the presence or absence of DOX treatment. These results recapitulate the tissue culture data and show that α9-nAChR overexpression in normal human breast epithelial cells sensitizes them such that they are transformed in response to nicotine exposure (FIG. 5, B, lanes 5 and 6). In vivo expression of α9-nAChR mRNA and protein was substantially induced in MCF-10A-Nic (DOX)-xenografted tumors, as detected by RT-PCR and western blot analyses after tumor dissection (FIG. 5, D) Immunohistochemical staining also revealed substantial induction of α9-nAChR expression in the MCF-10A-Nic (DOX−) tumors (FIG. 5, E).

It is difficult to provide direct evidence of smoking related α9-nAChR-mediated carcinogenic effects in human breast cancer. We performed an epidemiological cohort study to assess the clinical significance of α9-nAChR expression in different stages of breast tumors and to correlate it to smoking history among Taiwanese women. In the present study, 174 breast tumor patients were recruited for evaluation of tobacco smoking history, clinical staging criteria, and α9-nAChR mRNA expression analysis of tumor vs normal paired samples (Table 2). The results indicate that seven of 18 (38%) breast tumor tissues were diagnosed as later stages (3-4) in the smoker group. By contrast, a similar occurrence ratio was detected but shifted to early stage (0-1) tumors in the passive (19 of 52, 36.5%) and non-smoker groups (40 of 104, 38%). Furthermore, increased expression of α9-nAChR mRNA in tumor tissues from current smokers compared with those from non-smokers was found (6.62-fold vs 1.51-fold, difference=5.11-fold, 95% CI=2.67 to 7.55-fold, P=0.003). By contrast, a lower fold ratio of α9-nAChR mRNA expression was detected in tumor tissues from passive-smokers compared with non-smokers (2.81-fold vs 1.51-fold, difference=1.3-fold, 95% CI=0.79 to 1.81-fold, P=0.256). In the present study, direct evidence for the nicotinic binding activity of α9-nAChR in human breast cancer was also provided by a [³H]-nicotine binding assay (FIG. 1, F). These observations have led to the conclusion that nicotine binding to nAChR may play a direct role in the promotion and progression of human breast cancers.

TABLE 2

Demographic evaluation of tobacco smoking history, clinical staging criteria, and 9-nAChR mRNA expression fold ratios of tumor/normal paired samples.

| | Patient Characteristic | | |
|---|---|---|---|
| | Current Smokers (n = 18) | Passive Smokers (n = 52) | Nonsmokers (n = 104) |
| Clinical Breast Cancer Stage, No. (%) | | | |
| 0 | ND* | 3 (5.8) | 6 (5.8) |
| 1 | 3 (16.7) | 16 (30.8) | 34 (32.7) |
| 2 | 8 (44.4) | 26 (50) | 44 (42.3) |
| 3 | 6 (33.3) | 6 (11.5) | 20 (19.2) |
| 4 | 1 (5.6) | 1 (1.9) | ND |
| Relative α9-nAChR mRNA expression in tumor vs normal tissue, No. (ave. fold & 95% CI) | | | |
| <1 fold difference (Normal > Tumor) | 4 (.83, .42 to 1.24)† | 11 (.37, .17-.57) | 43 (.3, .01-.6) |
| 1-5 fold difference (Tumor > Normal) | 8 (2.87, 1.33 to 4.42) | 31 (2.59, 1.93-3.25) | 61 (2.37, 1.19-3.54) |
| >5 fold difference | 6 (15.5, 8.95 to 22.05) | 10 (6.22, 3.62-2.6) | ND |
| Total (Mean per group) | 18 (6.62, 3.66 to 9.58)‡ | 52 (2.81, 1.87-3.75) | 104 (1.51, .69-2.33) |

*ND = not determined.
†P = .008 for current vs nonsmokers in comparisons using two-sided nonparametric Kruskal-Wallis and Mann-Whitney tests.
‡†P = .003 for current vs nonsmokers in comparisons using two-sided nonparametric Kruskal-Wallis and Mann-Whitney tests. A P-value ≤.05 was considered to be statistically significant.

What is claimed is:

1. An siRNA molecule for suppressing expression of α9-nAChR gene via RNA interference (RNAi), which comprises: a sense strand having at least the sequence of SEQ ID NO: 1 or SEQ ID NO: 3 or a complementary sequence thereof having sufficient complementarity to an RNA of said α9-nAChR gene for the siRNA molecule to direct cleavage of said RNA via RNA interference.

2. The siRNA molecule of claim 1, wherein the complementary sequence has 70%, 80%, 90%, or 100% complementary to SEQ ID NO: 1 or SEQ ID NO:3.

3. The siRNA molecule of claim 1, wherein the complementary sequence has the sequences as shown in SEQ ID NO: 2 that is perfectly complementary to SEQ ID NO: 1 and SEQ ID NO: 4 that is perfectly complementary to SEQ ID NO: 3.

4. The siRNA molecule of claim 1, which is a sequence further comprising a hairpin loop region and a sequence complementary to SEQ ID NO: 1 or SEQ ID NO: 3, or a complementary sequence thereof having sufficient complementarity to an RNA of said α9-nAChR gene for the siRNA molecule to direct cleavage of said RNA via RNA interference.

5. The siRNA molecule of claim 4, which can be in linear for hairpin form.

6. The siRNA molecule of claim 4, wherein the hairpin loop region has 5, 6, 7, 8, 9, 10, 11, 12 or 13 nucleotides in length.

7. The siRNA molecule of claim 4, wherein the hairpin loop region is the sequence of TTCAAGAGA (SEQ ID NO:9) or TCTCTTGAA (SEQ ID NO:10).

8. The siRNA molecule of claim 4, which comprises the sequence as shown in SEQ ID NO: 5 and SEQ ID NO: 7.

9. The siRNA molecule of claim 4, wherein the complementary sequence has the sequences as shown in SEQ ID NO: 6 that is perfectly complementary to SEQ ID NO: 5 and SEQ ID NO: 8 that is perfectly complementary to SEQ ID NO: 7.

10. A pharmaceutical composition comprising a siRNA molecule of claim 1 and a pharmaceutically acceptable carrier.

11. A method of inhibiting and/or treating malignant progression of nicotine-derived-compound-induced breast cancer, comprising administering to a subject an α9-nAChR inhibitor in an amount effective to reduce α9-nAChR expression, wherein the α9-nAChR inhibitor is the siRNA molecule of claim 1, thereby treating and/or inhibiting and/or treating malignant progression of said breast cancer.

12. The method of claim 11, wherein the α9-nAChR inhibitor is administrated via oral, inhaled, buccal, parenteral, transdermal and routes or with a liposome.

13. The method of claim 11, wherein the dosage amounts of the α9-nAChR inhibitor ranges from 10 mg/kg/day to 500 mg/kg/day.

* * * * *